US011957481B2

(12) United States Patent
Stinton et al.

(10) Patent No.: US 11,957,481 B2
(45) Date of Patent: Apr. 16, 2024

(54) DEVICE AND METHOD FOR MONITORING PATIENT COMPLIANCE

(71) Applicant: ERMI LLC, Atlanta, GA (US)

(72) Inventors: Shaun Kevin Stinton, Chamblee, GA (US); Edward Dittmar, Marietta, GA (US); Thomas P. Branch, Atlanta, GA (US); T. Christopher Madden, Atlanta, GA (US)

(73) Assignee: ERMI LLC, Atlanta, GA (US)

( * ) Notice: Subject to any disclaimer, the term of this patent is extended or adjusted under 35 U.S.C. 154(b) by 1085 days.

(21) Appl. No.: 16/643,100

(22) PCT Filed: Feb. 21, 2020

(86) PCT No.: PCT/US2020/019292
§ 371 (c)(1),
(2) Date: Feb. 28, 2020

(87) PCT Pub. No.: WO2020/172572
PCT Pub. Date: Aug. 27, 2020

(65) Prior Publication Data
US 2021/0196191 A1    Jul. 1, 2021

Related U.S. Application Data

(60) Provisional application No. 62/808,552, filed on Feb. 21, 2019.

(51) Int. Cl.
*A61H 1/02*    (2006.01)
*A61B 5/00*    (2006.01)
*A61B 5/11*    (2006.01)

(52) U.S. Cl.
CPC .......... *A61B 5/4833* (2013.01); *A61B 5/1121* (2013.01); *A61B 5/7405* (2013.01);
(Continued)

(58) Field of Classification Search
CPC .......................................... A61H 1/0237–0296
See application file for complete search history.

(56) References Cited

U.S. PATENT DOCUMENTS 4,971,043 A * 11/1990 Jones .................... A61H 1/0218
602/36
6,152,855 A * 11/2000 Dean, Jr. .............. A61H 1/0262
601/24

(Continued)

FOREIGN PATENT DOCUMENTS

JP    2019500928    1/2019
WO    2018183386    10/2018

OTHER PUBLICATIONS

Patent Cooperation Treaty; International Search Report and Written Opinion cited in PCT/US2020/019292 dated Jul. 31, 2020; 13 pages.

(Continued)

*Primary Examiner* — Michael J Tsai
(74) *Attorney, Agent, or Firm* — Shumaker, Loop & Kendrick, LLP; Patrick B. Horne

(57)    ABSTRACT

Disclosed are a joint manipulation device and system for increasing the range of motion of a joint of a user, and monitoring the compliance of the user's operation of the joint manipulation device to standards or guidelines set by a monitoring entity. Certain sensors associated with the joint manipulation device may cause an indicator to transmit an alert to the user based on whether or not the device is sufficiently engaged with a limb or joint of the user to be considered in compliance. Additionally, progress data associated with the range of motion of the user's joint may be obtained by a sensor assembly and transmitted to one or more systems associated with the device system. Progress data obtained during a period of non-compliant use of the device may be excluded from the transmitted data, thereby (Continued)

generating a set of compliant progress data for accurate analysis of device effectiveness.

27 Claims, 18 Drawing Sheets

(52) U.S. Cl.
CPC .............. *A61B 5/746* (2013.01); *A61H 1/02* (2013.01); *A61H 1/024* (2013.01); *A61H 1/0281* (2013.01); *A61H 2201/1238* (2013.01); *A61H 2201/501* (2013.01); *A61H 2201/5043* (2013.01); *A61H 2201/5061* (2013.01); *A61H 2201/5064* (2013.01); *A61H 2201/5069* (2013.01); *A61H 2201/5071* (2013.01); *A61H 2201/5084* (2013.01)

(56) References Cited

U.S. PATENT DOCUMENTS

| | | | | |
|---|---|---|---|---|
| 6,827,670 | B1* | 12/2004 | Stark | A61H 1/00 482/8 |
| 9,566,004 | B1* | 2/2017 | Radwin | A61B 5/0002 |
| 2005/0054957 | A1* | 3/2005 | Yamazaki | A61H 23/0245 601/46 |
| 2005/0209538 | A1* | 9/2005 | Lev | A61H 7/007 601/87 |
| 2006/0079817 | A1* | 4/2006 | Dewald | A63B 21/4019 482/901 |
| 2009/0048081 | A1* | 2/2009 | Kamins | A63B 21/153 600/595 |
| 2009/0227925 | A1* | 9/2009 | McBean | A61H 1/008 602/16 |
| 2013/0171599 | A1* | 7/2013 | Bleich | A63B 24/0062 434/247 |
| 2014/0277582 | A1* | 9/2014 | Leuthardt | A61B 5/0006 623/25 |
| 2015/0297934 | A1* | 10/2015 | Agrawal | A61H 1/0266 482/4 |
| 2015/0360069 | A1* | 12/2015 | Marti | A63B 23/1272 482/7 |
| 2016/0140319 | A1* | 5/2016 | Stark | A63B 24/00 434/362 |
| 2016/0143593 | A1 | 5/2016 | Fu et al. | |
| 2016/0324727 | A1 | 11/2016 | Waugh et al. | |
| 2019/0001174 | A1* | 1/2019 | Marti | A63B 21/0023 |
| 2020/0061414 | A1* | 2/2020 | Gillis | A63B 21/00061 |
| 2021/0282956 | A1* | 9/2021 | Di Pardo | A61B 5/6812 |

OTHER PUBLICATIONS

Patent Cooperation Treaty; International Preliminary Report on Patentability cited in application No. PCT/US2020/019292 dated Aug. 10, 2021; 8 pages.

\* cited by examiner

DEVICE AND METHOD FOR MONITORING PATIENT COMPLIANCE

FIELD OF THE INVENTION

The present invention is generally directed to a device and method for providing a device configured to provide range of motion stretches and exercises on one or more joints of a patient, such that the patient's compliance with use instructions can be assessed and monitored.

BACKGROUND

Joint manipulation devices such as knee extension devices, knee flexion devices, elbow extension and flexion devices, shoulder rotation devices, and the like, are useful in helping a user restore lost range of motion in a joint after an injury or surgery. Many of these devices are either mobile or installed in a home of a user, such that the user is operating the device without immediate supervision of the entity providing the device or recommending the joint exercise with the joint manipulation device. Therefore, it is difficult for a managing entity (an entity that provides the device, that recommends the device as part of a medical treatment, that covers the device for insurance purposes, and the like), to know whether the device is being used as intended or instructed. Measuring the patient's progress in restoring range of motion is also a key component in their recovery. If the device is not being used properly, this should be corrected as soon as possible, and if the device is not effective in restoring range of motion for a particular patient, then a different treatment modality can be initiated in a timely manner.

Therefore, a need exists to provide a joint manipulation device that measures aspects of a user's operation of the joint manipulation device and tracks the frequency and duration of the user's operation of the joint manipulation device. Furthermore, a need exists to provide such a device that can also transmit recorded aspects of the user's operation of the joint manipulation device, and allow a managing entity or other third party to adjust aspects of the joint manipulation device or the instructions to the user over time.

BRIEF SUMMARY

The following presents a summary of certain embodiments of the invention. This summary is not intended to identify key or critical elements of all embodiments nor delineate the scope of any or all embodiments. Its sole purpose is to present certain concepts and elements of one or more embodiments in a summary form as a prelude to the more detailed description that follows.

Embodiments of the present invention address the above needs and/or achieve other advantages by providing apparatuses (e.g., a system, computer program product and/or other devices) and methods for monitoring patient compliance with the intended or appropriate use of a joint manipulation device. The system embodiments may comprise one or more memory devices having computer readable program code stored thereon, a communication device, and one or more processing devices operatively coupled to the one or more memory devices, wherein the one or more processing devices are configured to execute the computer readable program code to carry out the invention. In computer program product embodiments of the invention, the computer program product comprises at least one non-transitory computer readable medium comprising computer readable instructions for carrying out the invention. Computer implemented method embodiments of the invention may comprise providing a computing system comprising a computer processing device and a non-transitory computer readable medium, where the computer readable medium comprises configured computer program instruction code, such that when said instruction code is operated by said computer processing device, said computer processing device performs certain operations to carry out the invention.

For sample, illustrative purposes, system environments will be summarized. The system may involve receiving compliance data from a joint manipulation device system associated with compliant operation of a joint manipulation device by a user, and comparing the received compliance data with predetermined compliant conditions. In some embodiments, the system may include providing an indication of a compliant status to the user at an indicator based on the comparison of the received compliance data and the predetermined compliant conditions. Furthermore, the system may include receiving progress data from the joint manipulation device system, wherein the progress data comprises at least one of pressure data, force data, time data, and range of motion data associated with a joint of the user. The system may then, in some embodiments, aggregate the received progress data into effectiveness data, wherein progress data collected during a period of non-compliance is excluded from the effectiveness data. In response to aggregating the received progress data into effectiveness data, the system may then transmit the effectiveness data to one or more third party systems.

In some embodiments of the system, providing an indication of a compliant status to the user at an indicator based on the comparison of the received compliance data and the predetermined compliant conditions further comprises determining that the received compliance data does not meet the predetermined compliant conditions, and transmitting control signals configured to cause a speaker device associated with the joint manipulation device system to emit a first audible alert to the user, wherein the first audible alert is associated with non-compliant use of the joint manipulation device. In some embodiments, a visual alert (e.g., a notification on a display of the joint manipulation device, a notification on a display of a mobile device of the user, a signal from a light emitting diode (LED) display, and the like) may be provided to the user in combination with, or instead of, the first audible alert.

In some embodiments, the compliance data and the progress data are received by the system from the joint manipulation device system. In some embodiments, the system comprises a mobile device running an application for receiving the compliance data and progress data as inputs self-reported by the user. In some such embodiments, the range of motion data comprises a minimum and a maximum degree of rotation for the joint of the user, as measured from one or more pictures taken by the user using the application running on the mobile device.

Furthermore, in some embodiments of the system, providing an indication of a compliant status to the user at an indicator based on the comparison of the received compliance data and the predetermined compliant conditions further comprises determining that the received compliance data does meet the predetermined compliant conditions, and transmitting control signals configured to cause a speaker device associated with the joint manipulation device system to emit a second audible alert to the user, wherein the second audible alert is associated with compliant use of the joint manipulation device.

In some embodiments of the system, the compliance data comprises at least a pressure exerted between a limb engaging member of the joint manipulation device and a portion of a limb of the user associated with the joint of the user. In some such embodiments, the compliance data meets the predetermined compliant conditions when the pressure exerted between the limb engaging member of the joint manipulation device and the portion of the limb of the user associated with the joint of the user is at or above a predetermined threshold pressure value.

The system may also include embodiments where the range of motion data comprises a minimum and a maximum degree of rotation for the joint of the user, as measured by one or more sensors of the joint manipulation device system. Additionally, the system may include embodiments where the time data comprises one or more periods of time during which the joint manipulation device system was operated in compliance with the predetermined compliant conditions.

The compliance could also be monitored via an app running on a smart phone or other mobile device with self-reported therapy times or with a timer incorporated with the app.

Finally, in some embodiments of the invention, the effectiveness data is transmitted to one or more doctors, physical therapists, and/or insurance provider organizations associated with the user or the joint manipulation device system.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
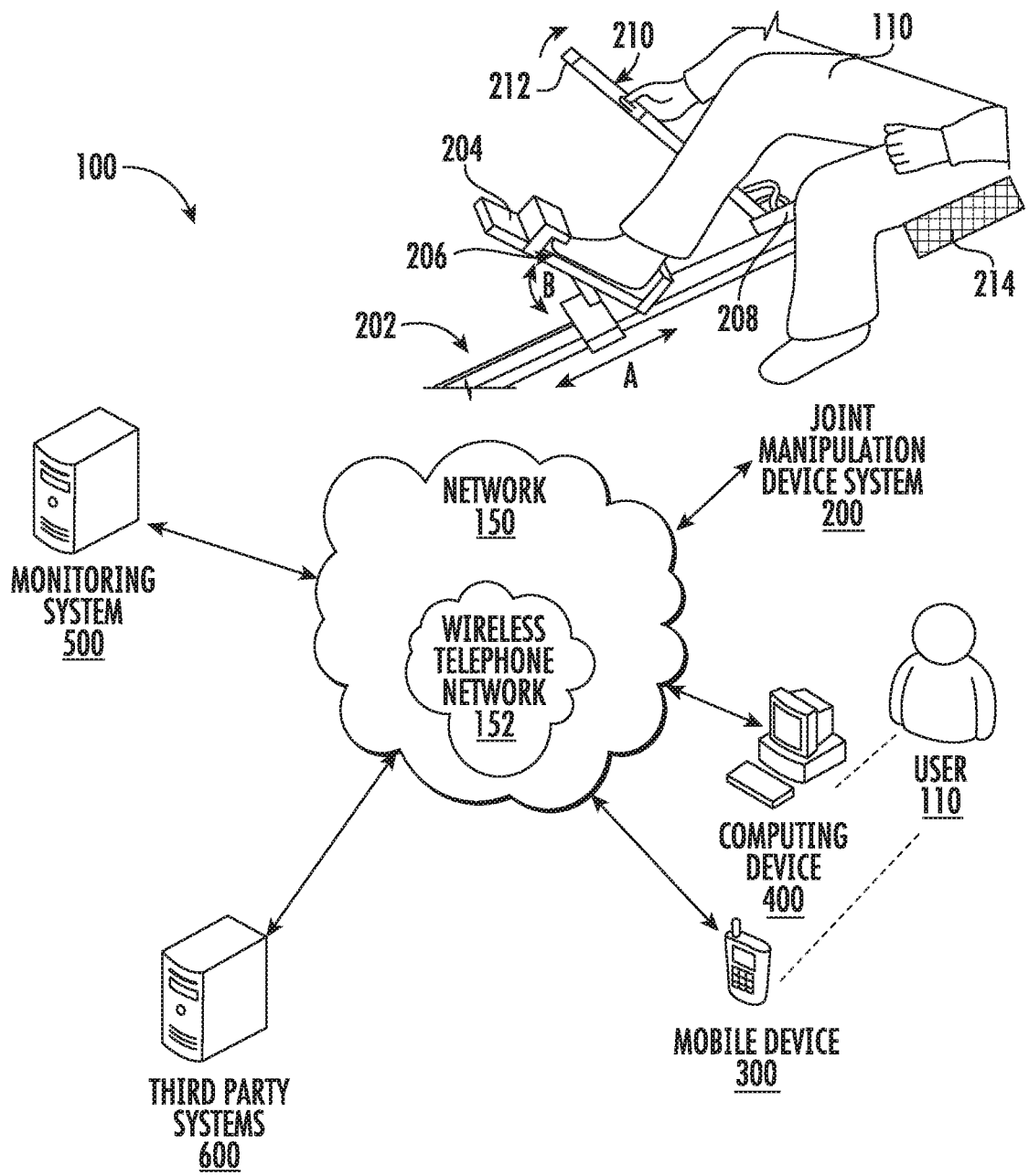
Figure 2A:
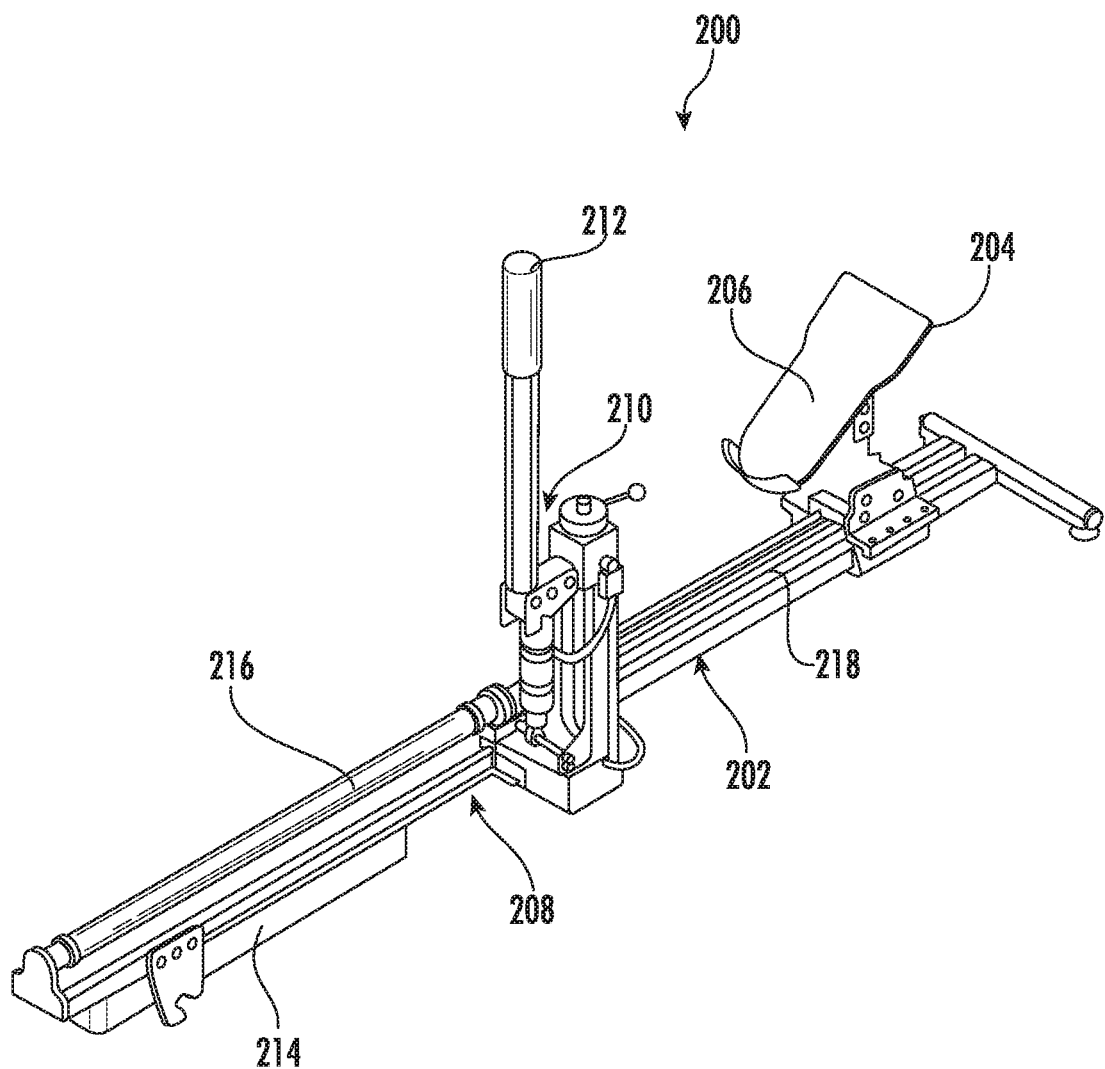
Figure 2B:
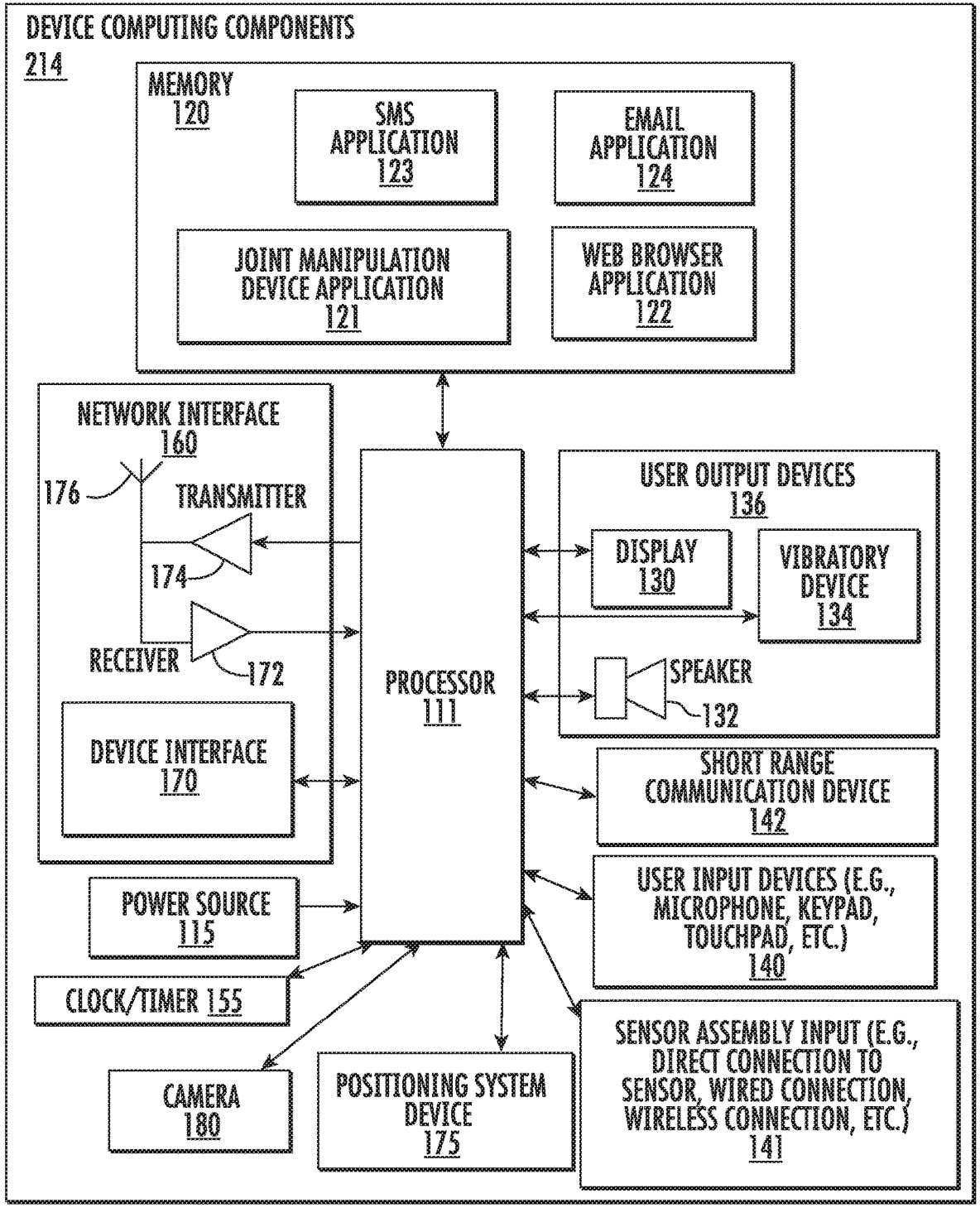
Figure 2C:
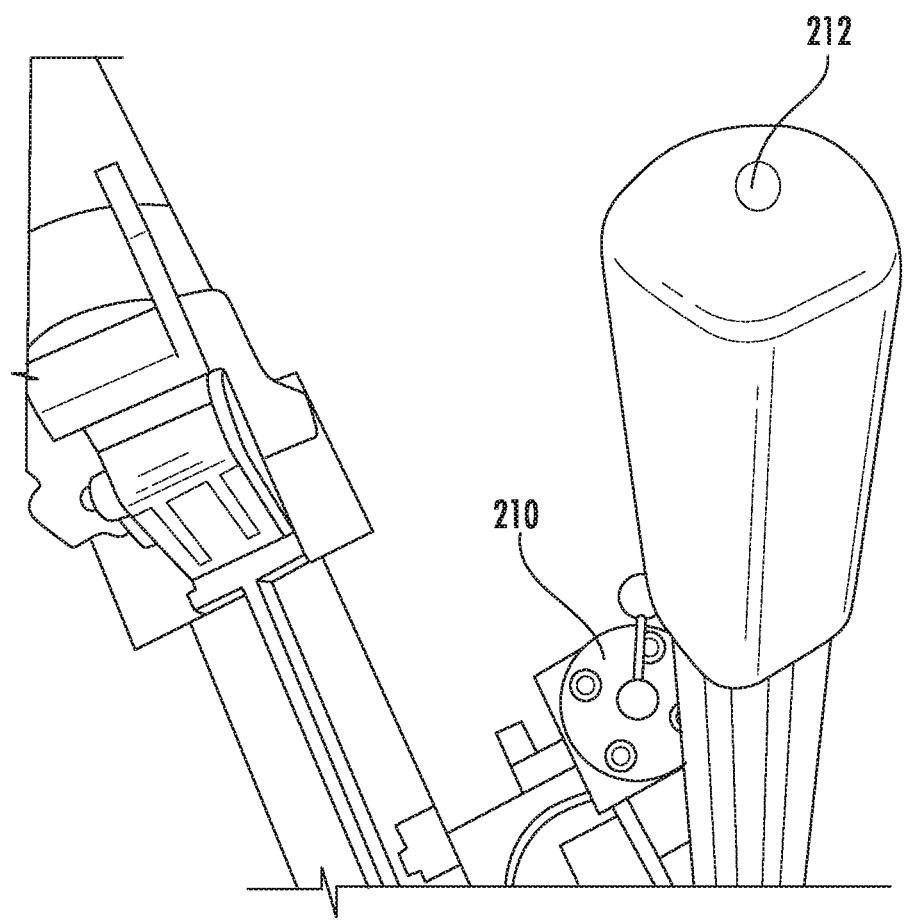
Figure 2D:
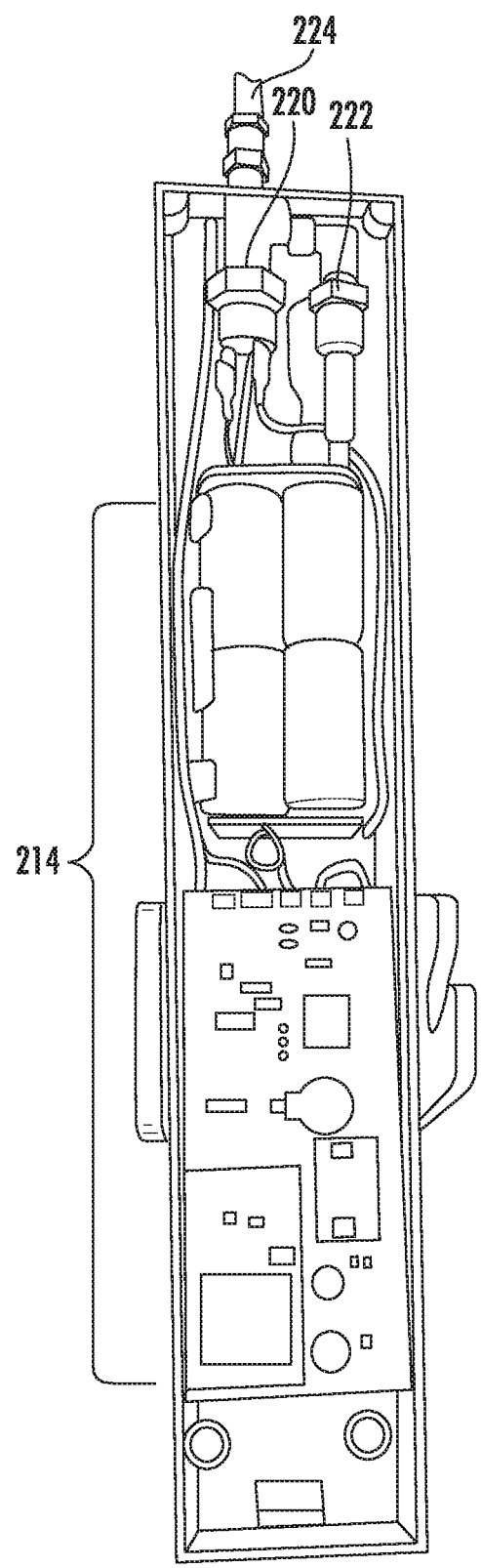
Figure 2E:
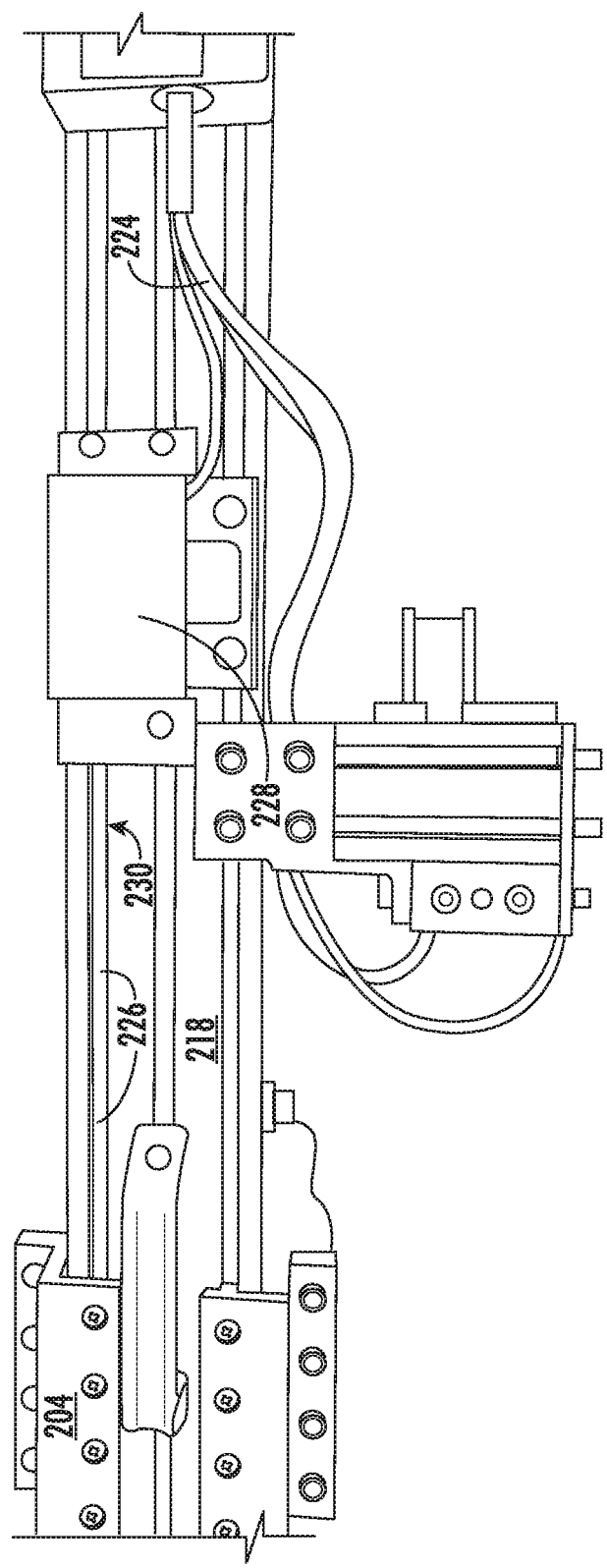
Figure 2F:
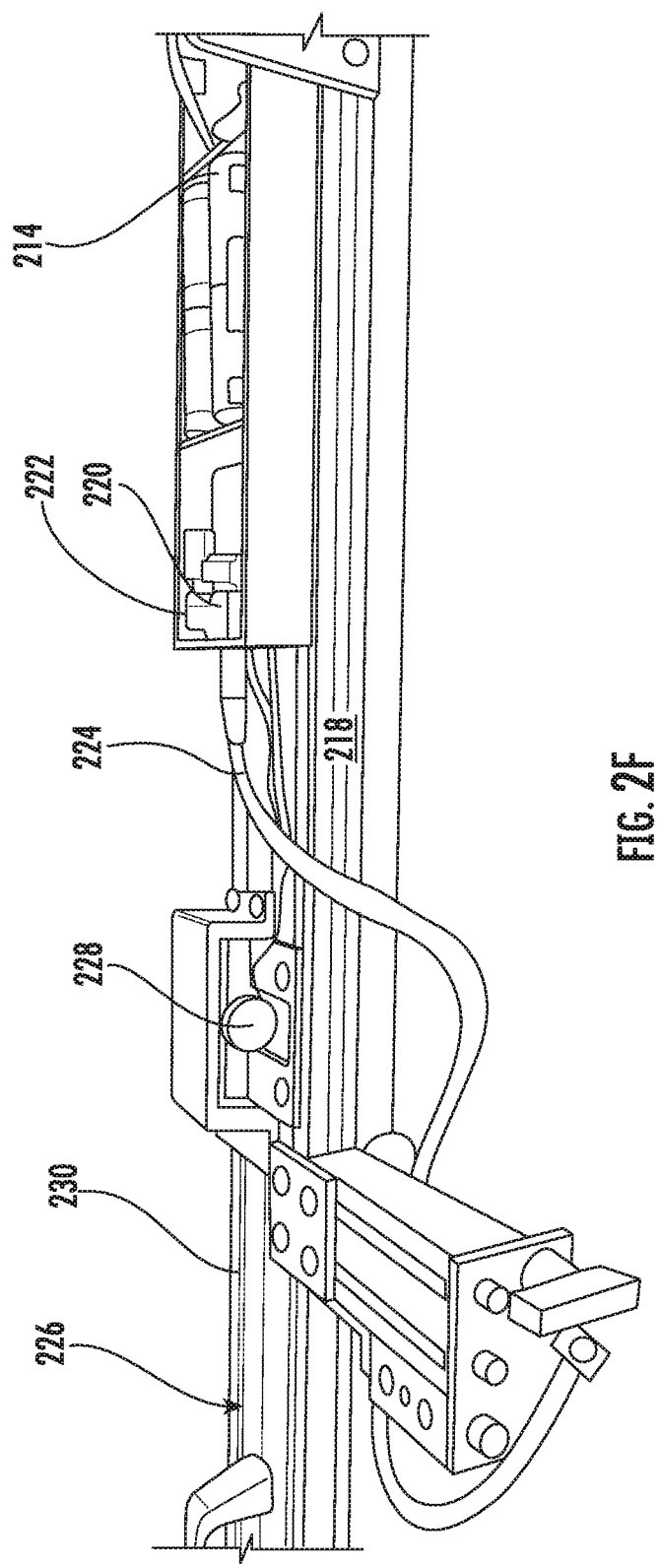
Figure 2G:
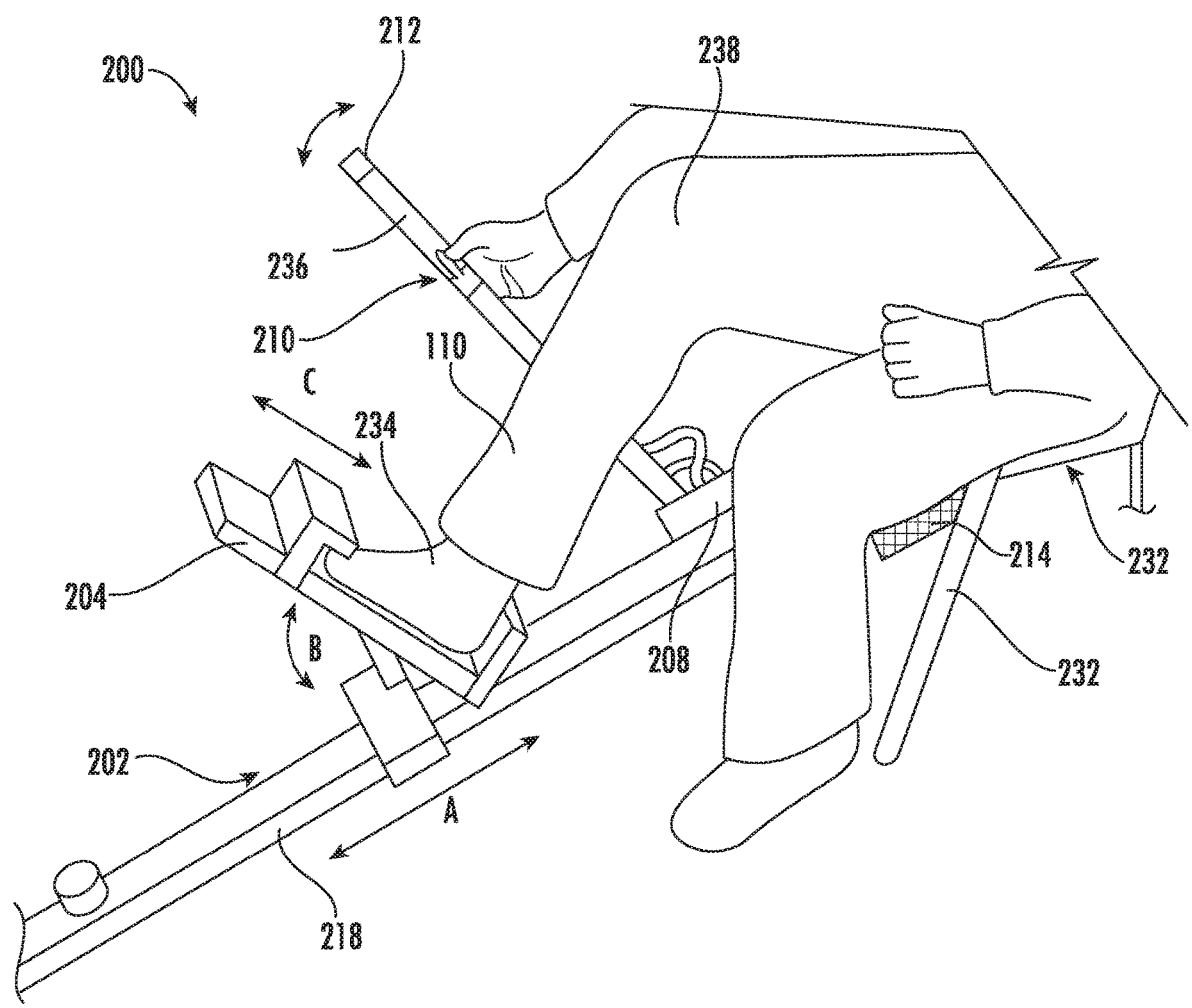
Figure 2H:
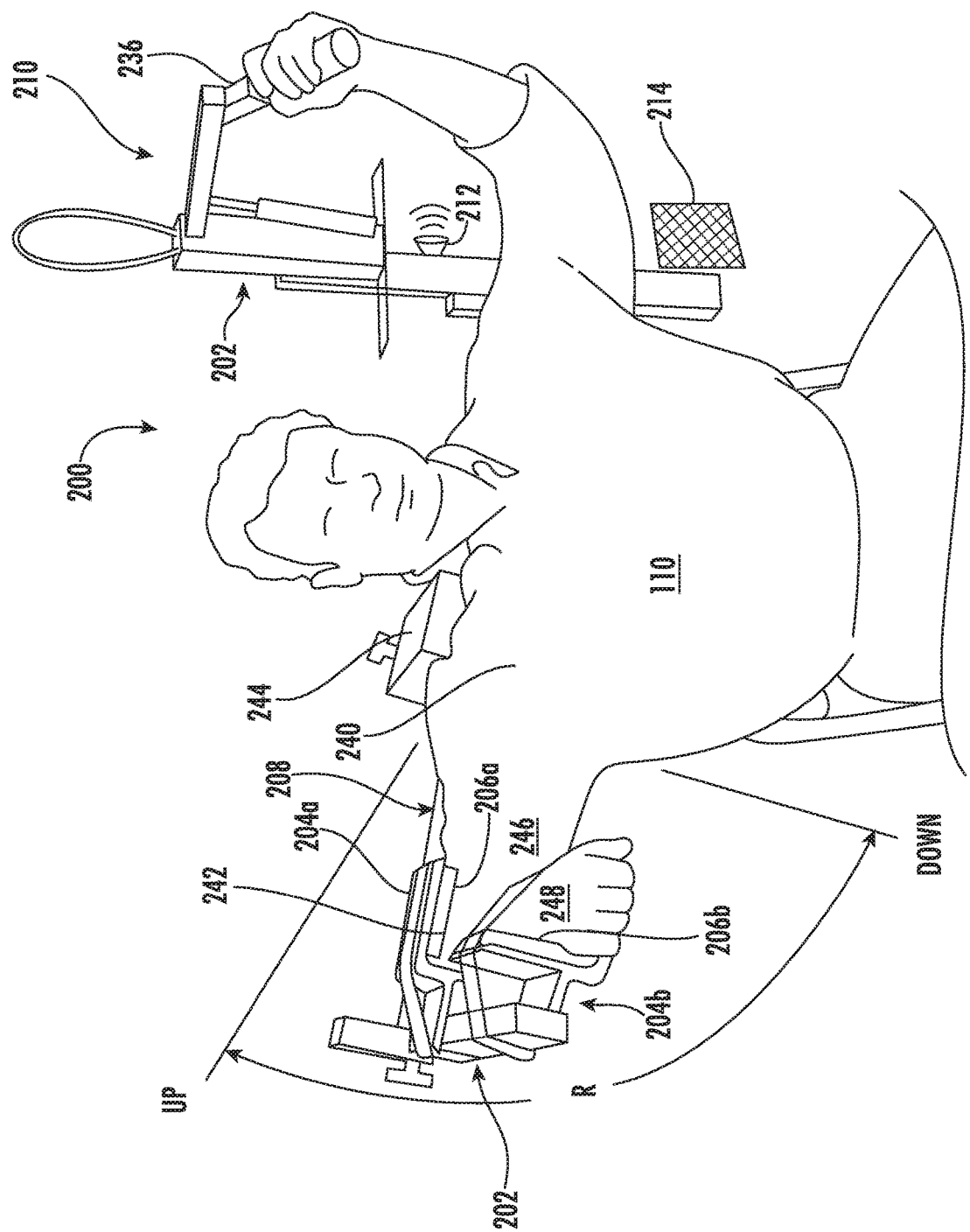
Figure 21:
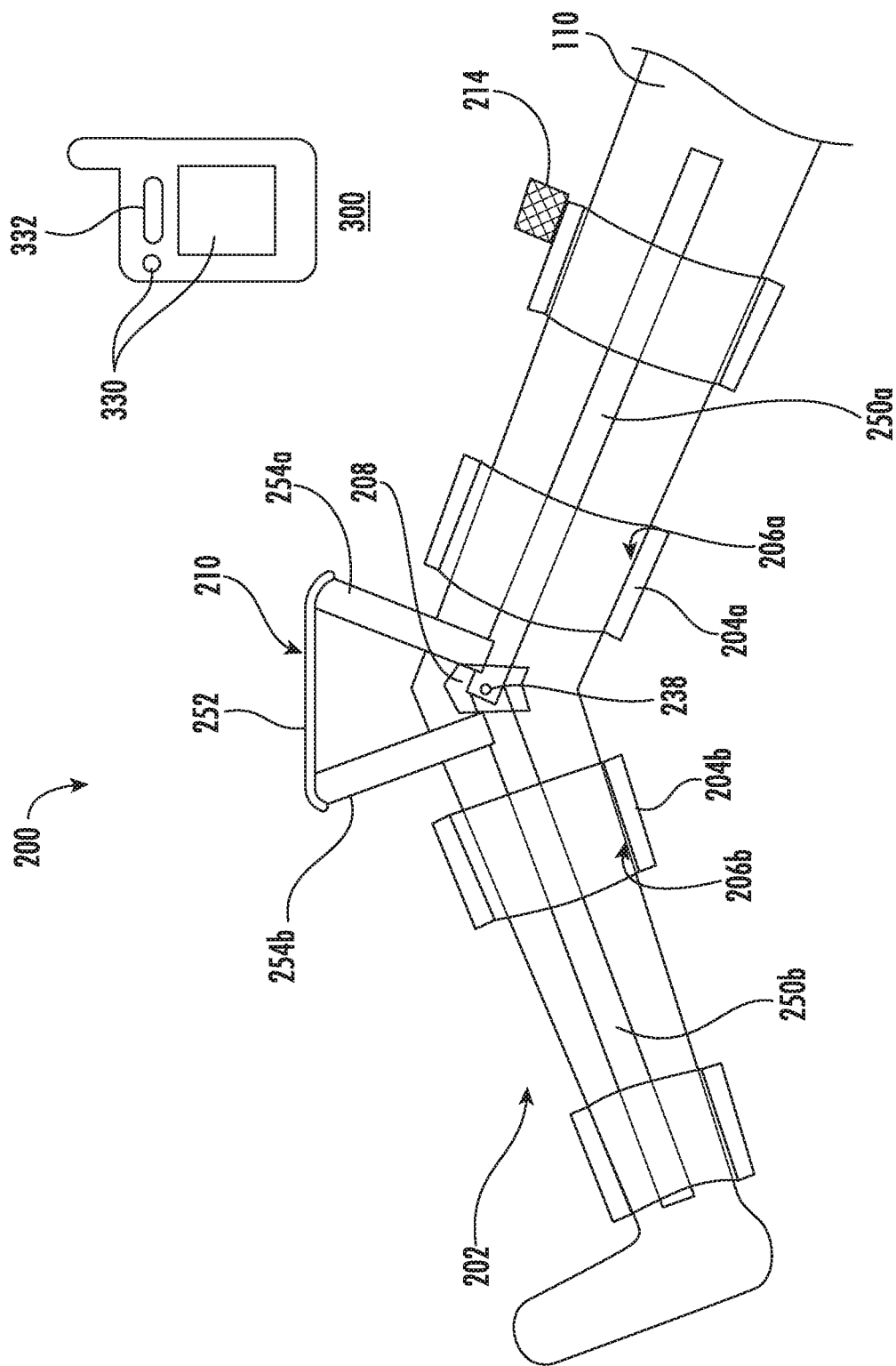
Figure 2J:
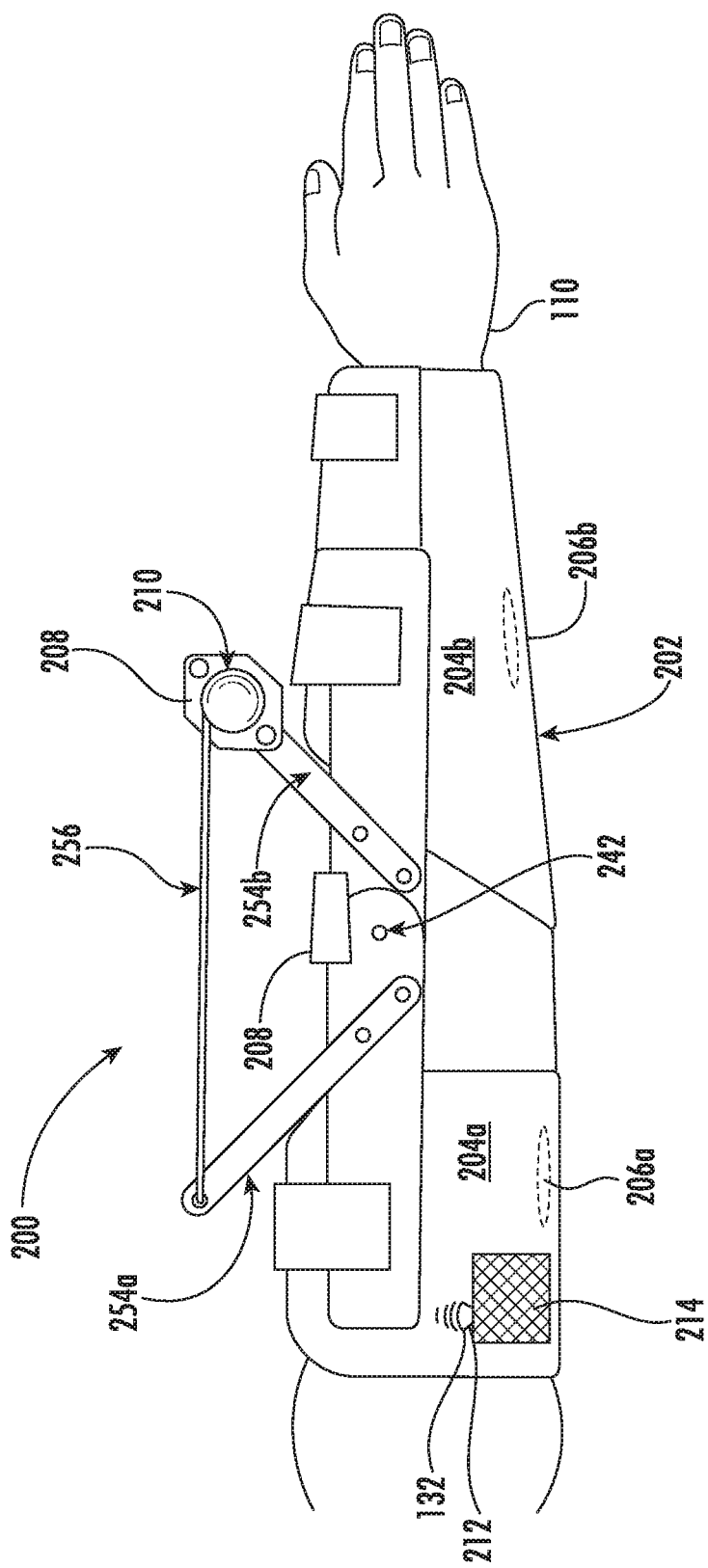
Figure 2K:
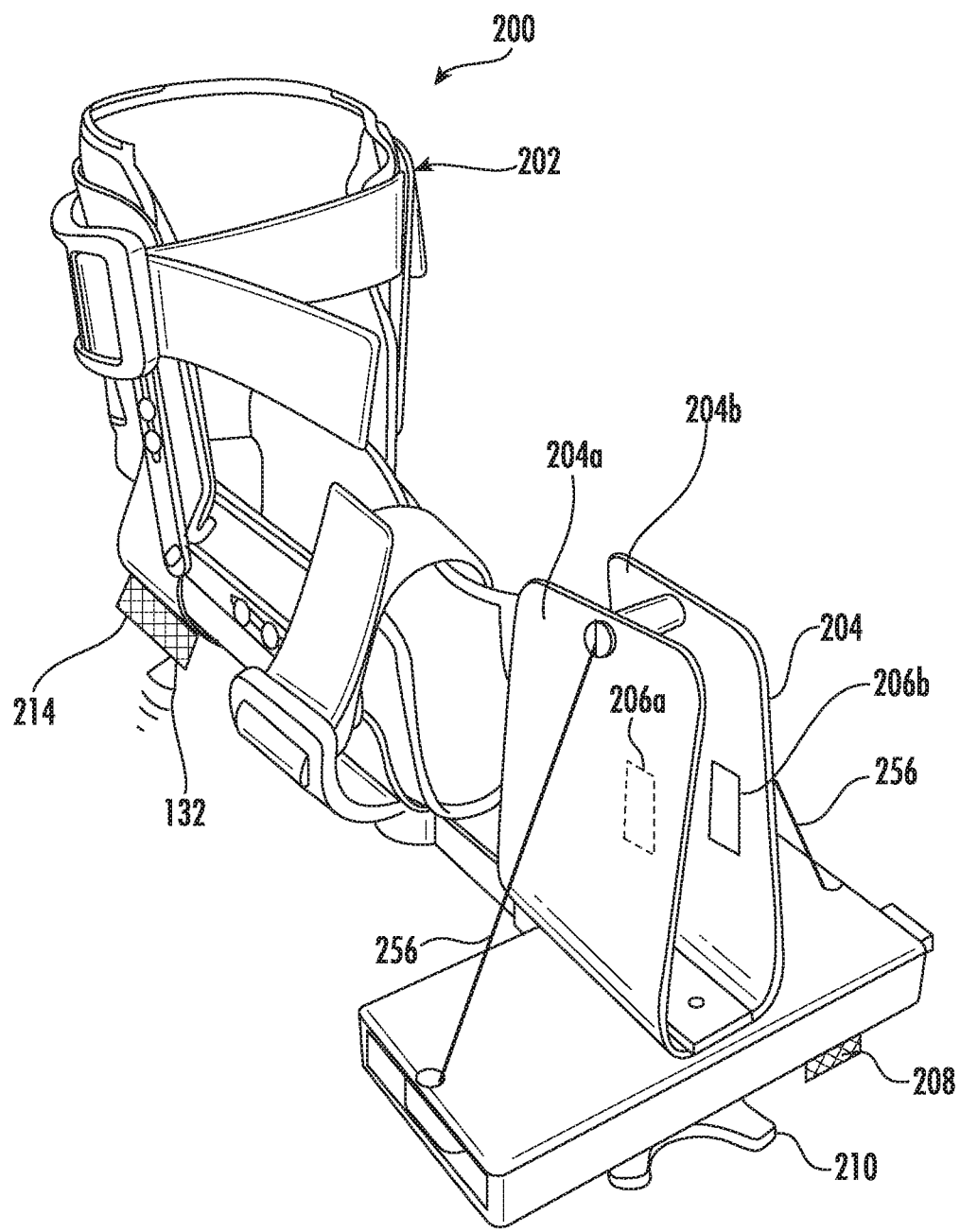
Figure 3:
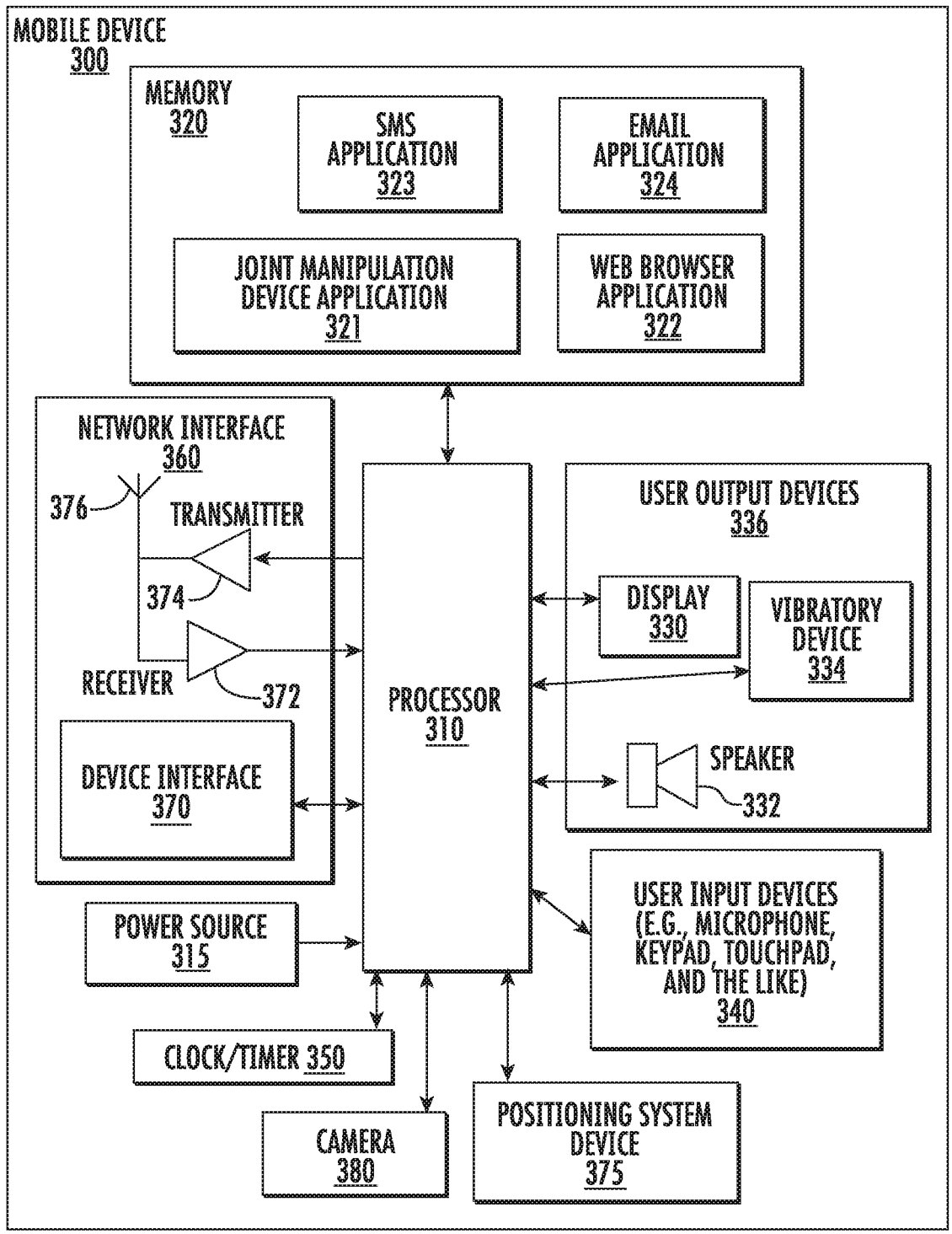
Figure 4:
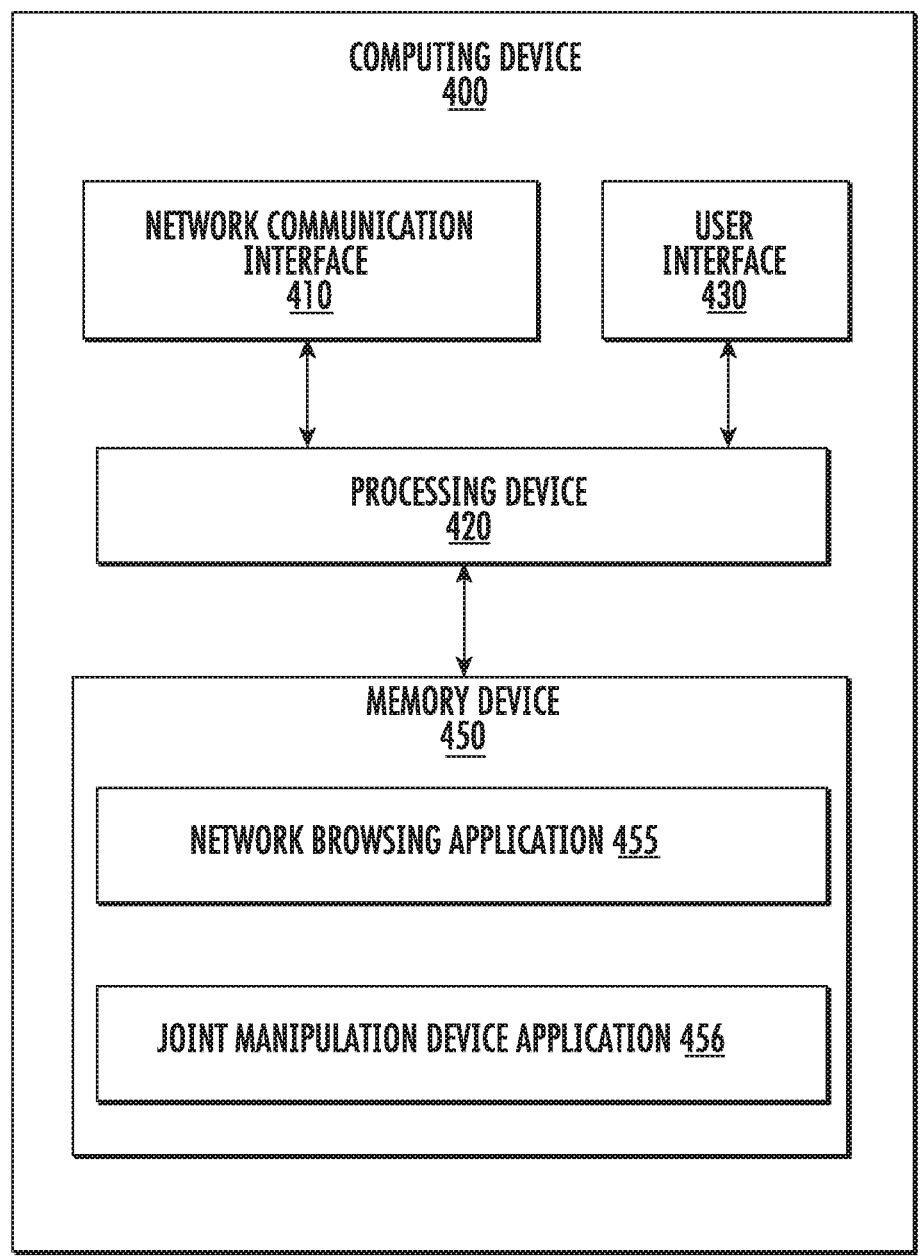
Figure 5:
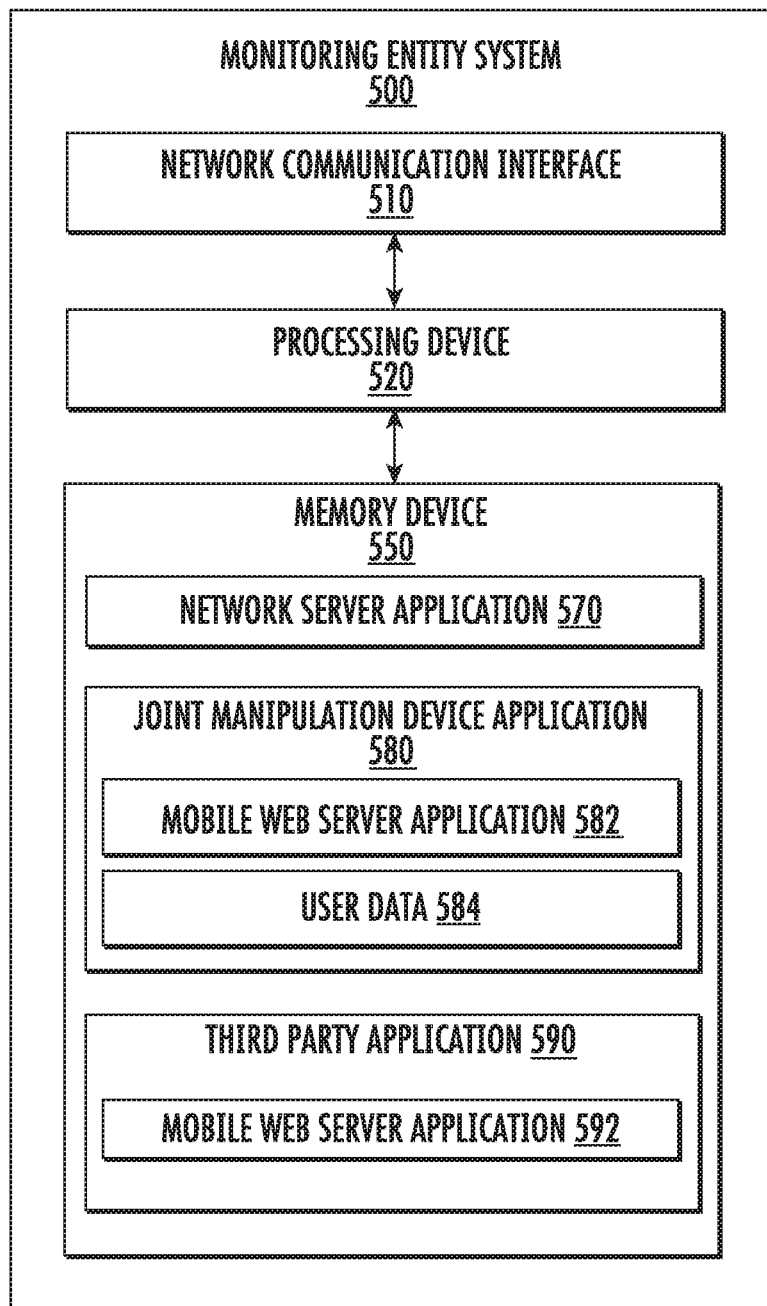
Figure 6:
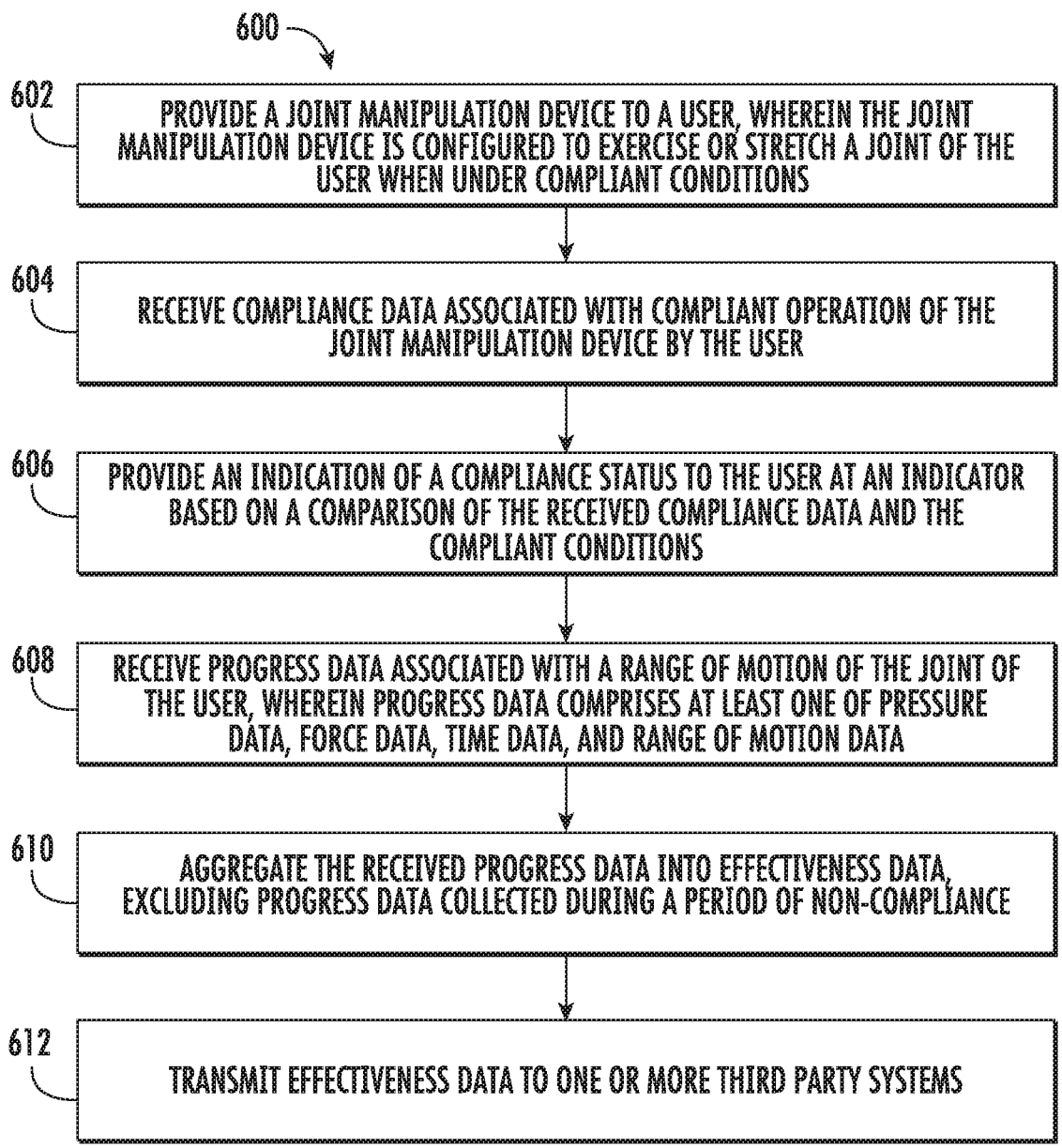
Figure 7A:
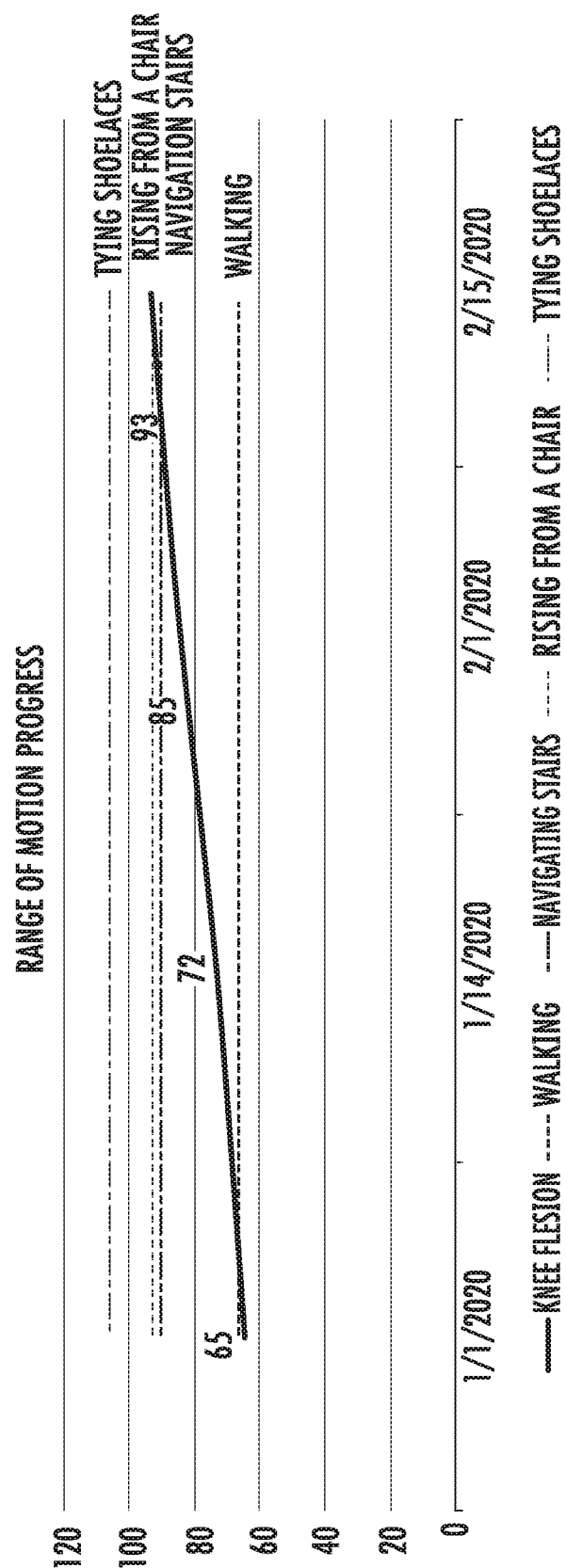
Figure 7B:
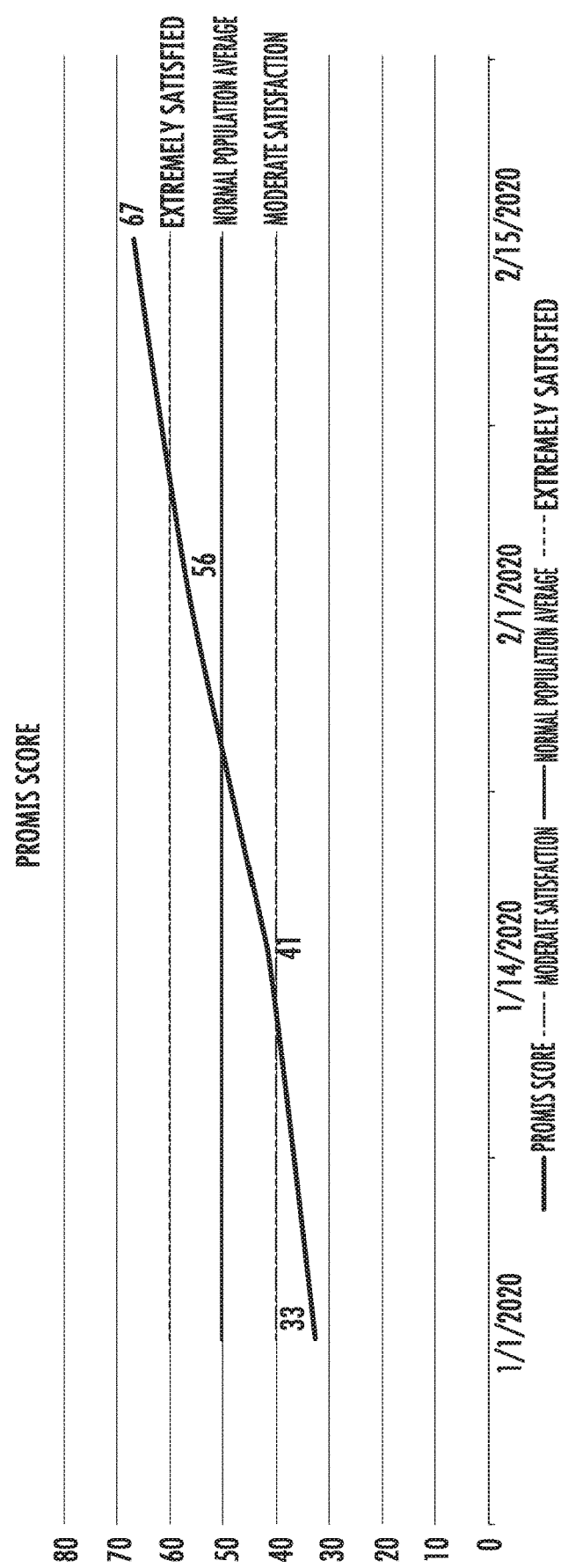

Having thus described embodiments of the invention in general terms, reference will now be made the accompanying drawings, wherein:

FIG. 1 provides a block diagram illustrating a system environment for providing and monitoring a joint manipulation device, in accordance with embodiments of the invention;

FIG. 2A provides a perspective view of one embodiments of a joint manipulation device of FIG. 1, in accordance with an embodiment of the invention;

FIG. 2B provides a block diagram illustrating the computing components of the joint manipulation device system of FIG. 1, in accordance with an embodiment of the invention;

FIG. 2C provides a close-up view of one embodiment of an indicator, in accordance with embodiments of the invention;

FIG. 2D provides a bottom view of a joint manipulation device and an accompanying sensor assembly, in accordance with embodiments of the invention;

FIG. 2E provides a bottom view of a joint manipulation device and accompanying sensor assembly, in accordance with embodiments of the invention;

FIG. 2F provides a perspective view of a joint manipulation device and an accompanying sensor assembly and device computing components, in accordance with embodiments of the invention;

FIG. 2G provides a perspective view of one embodiments of a joint manipulation device of FIG. 1, in accordance with an embodiment of the invention;

FIG. 2H provides a perspective view of one embodiments of a joint manipulation device of FIG. 1, in accordance with an embodiment of the invention;

FIG. 2I provides a perspective view of one embodiments of a joint manipulation device of FIG. 1, in accordance with an embodiment of the invention;

FIG. 2J provides a perspective view of one embodiments of a joint manipulation device of FIG. 1, in accordance with an embodiment of the invention;

FIG. 2K provides a perspective view of one embodiments of a joint manipulation device of FIG. 1, in accordance with an embodiment of the invention;

FIG. 3 provides a block diagram illustrating the mobile device of FIG. 1, in accordance with embodiments of the invention;

FIG. 4 provides a block diagram illustrating the computing device of FIG. 1, in accordance with embodiments of the invention;

FIG. 5 provides a block diagram illustrating the monitoring entity system of FIG. 1, in accordance with embodiments of the invention;

FIG. 6 provides a flowchart illustrating a process for monitoring a user's compliance with a joint manipulation device, in accordance with embodiments of the invention;

FIG. 7A is a graph illustrating a hypothetical patient's range of motion progress; and FIG. 7B is a graph illustrating a hypothetical PROMIS patient progress score over time.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on." Like numbers refer to like elements throughout.

As used herein, a "joint manipulation device" may be any device configured to exercise a joint of a human body. In some embodiments, the joint manipulation device may be especially configured to stretch tissue around a joint after a surgery of the joint, increasing the range of motion for the joint by breaking up scar tissue resulting from the surgery.

For example, a joint manipulation device may be a knee extension and/or device configured to stretch a leg such that the knee joint of the leg rotates in extension and/or in flexion. In some embodiments, the joint manipulation device may be the knee extension device described in U.S. Pat. No. 7,479,121, or a similar apparatus for enabling the movement of human limbs.

Likewise, in some embodiments, the joint manipulation device may be a shoulder extension control device, such as the shoulder extension control device described in U.S. Pat. No. 7,547,289.

The joint manipulation device may comprise a joint manipulation assembly that causes the movement of portions of the limb about the targeted joint. This joint manipulation assembly may be manually powered (e.g., by the user exerting a force on one or more of the user's limbs, by the user operating a lever or pump, by the user turning a dial, and the like), automatically powered (e.g., the device may be automatically configured to apply certain forces or resistive forces upon one or more limbs of the user in a single direction or in multiple directions over time), and/or powered by a third party such as a managing entity (e.g., a healthcare provider may transmit control signals to the device configured to cause the device to apply certain forces to one or more limbs of the user based on a rehabilitation plan).

Embodiments of the present invention provide a system and method for providing, monitoring, and/or adjusting a joint manipulation device. The joint manipulating device may comprise at least one limb engaging member. The limb engaging member may be embodied as a foot rest, a leg brace, an arm brace, a wrist brace, a should or upper arm brace, an ankle brace, and/or the like, so long as at least a portion of the limb engaging member engages the limb and/or joint of a user at some point. Additionally or alternatively, the limb engaging member may be any device configured to cause one limb to move with respect to another limb. For example, a limb engaging member may engage a tibia of a user, and rotate the tibia with respect to the femur of the same leg, where the femur is either held in a stationary position or also allowed to move. In some embodiments, the limb engaging member causes one or more limbs of the user to rotate around, slide across, pull away from, press towards, and/or twist with respect to an associated joint. The limb engaging member can be manipulated by a joint manipulation assembly operatively coupled to the limb engaging member. For example, the joint manipulation assembly may be a hydraulic drive system, a ratcheting system, a lever system, a pulley system, or any other system configured to move at least a portion of the limb engaging member such that a limb of the user is rotated or otherwise moved relative to a joint of the user.

One or more sensors can be operatively coupled to the joint manipulation device to measure certain aspects of the joint manipulation device and the user's operation of the joint manipulation device on a joint of the user. In some embodiments, a force sensor (e.g., a pressure sensor) is operatively coupled to at least a portion of the limb engaging member, to measure a force exerted upon the device (and therefore also exerted upon the limb and/or joint of the user). This force sensor may contain and/or comprise a force switch (e.g., a pressure switch) that is configured to transmit a signal to one or more components of the joint manipulation device or and/or any systems associated with the joint manipulation device when the force switch changes its orientation due to a certain threshold force being met. For example, in some embodiments, the force switch is configured to turn on certain electronic components of the joint manipulation device (or transform the electronic components from a low energy state to an activated state) once the force threshold is met or passed. In this way, the electronic components of the joint manipulation device can begin to record data associated with the user's operation of the joint manipulation device (e.g., time of operation, duration of operation, force applied to one or more portions of a user's limb, distance of movement of a limb of the user, rotation of portions of a limb about a joint, and the like).

Additionally or alternatively, when the force switch determines that the measured force value is above the force threshold, the system may cause an indicator to display an indication to the user (e.g., a light-emitting diode ("LED") signal, a notification on a mobile device associated with the user, a notification on a display screen associated with the joint manipulation device, an audible signal, and the like) that the user is appropriately engaging the joint manipulation device.

The force switch and the indicator may also be configured such that when the force measured or received by the force switch falls below the force threshold, the indicator will then automatically, or after a predetermined period of time, transform to indicate that the user is no longer appropriately engaging the joint manipulation device. For example, when the joint manipulation device is engaging the user and applying a desired force, the force switch is triggered and an LED associated with the joint manipulation device may emit a green light. But when the force of the joint manipulation device upon the limb of the user falls below the threshold amount, the LED emits a yellow light. Furthermore, after the force threshold is not met for one minute, the LED may change to emit a red light. These lights can help a user determine whether the device is being used properly or as instructed, where the user is notified that the force should be increased to meet the desired exercise routine for the joint.

The joint manipulation device may also house computing components for receiving signals from the sensors, transforming the signals from the sensors into calibrated measurements, storing measurements, and/or transmitting measurement data to one or more systems over a network. In some embodiments, the computing components of the joint manipulation device may be configured to receive input (e.g., target forces to be applied to a limb or joint of a user, target angles or orientations of a joint of the user, target timing for the user's operation of the joint manipulation device, and the like) from a monitoring or managing entity, or from a healthcare agent associated with the user or the joint manipulation device.

In some embodiments, the computing components of the joint manipulation device may be configured to control one or more aspects of the joint manipulation assembly that causes movement or the application of force upon the limb and/or joint of the user. For example, the computing components may be configured to automatically apply a sliding force, a rotational force, and/or a resistive force to a portion of the limb of a user such that the user's joint associated with the limb is stretched to a desired or targeted degree. This targeted degree can be set by the user of the device, through a computing device of the user connected to the computing components of the joint manipulation device through a network, or by a third party such as a monitoring entity or a medical entity.

In some embodiments, the device is configured to communicate with a mobile device or other computing device or monitor associated with the user, such that the device can transmit information about the user's operation of the joint manipulation device and the user's progress in conducting exercises with the joint manipulation device over a period of time. For example, the data transmitted by the joint manipulation device may populate in a mobile application installed on the mobile device of the user (or installed on a third party server and accessed at a web page). In this way, the user can view details of specific joint exercises and/or the user's progress over time in using the joint manipulating device to stretch and exercise the user's joint. The app can also provide feedback to the patient related to their progress and compare the progress to milestones such as the range of motion needed for performing activities of daily living such as walking, navigating stairs, rising from a chair, etc. This could provide motivation for the patient to continue using the device to reach the next target.

Furthermore, the device can be configured to transmit data associated with the device to one or more third party entities for record keeping and monitoring purposes. For example, some managing or monitoring entities may desire to track the specific and/or total usage of the joint manipulation device by a user for healthcare (e.g., physical therapy), health insurance, and scientific (e.g., effectiveness studies for the joint manipulation device) purposes.

The joint manipulating device may also comprise a global positioning system ("GPS") that can be tracked by the managing or monitoring entity to locate the device if needed.

As an example of the possible functioning and monitoring capabilities of the joint manipulation device system, a brief description of a possible operation of the system will now be described herein. A monitoring entity that is associated with a monitoring system may provide a joint manipulation device to a user as part of the user's rehabilitation plan to improve the range of motion in a joint of the user. The joint manipulation device may be configured to stretch the joint of the user by exerting forces upon portions of the user's limb(s) near the injured joint, thereby breaking up scarred or injured tissue and ligaments around the joint, and causing the joint to be able to increase its range of motion. However, the joint manipulation device may need to be operated in a specific manner. For example, it may need to be operated such that at least a certain force threshold is applied to the limb and/or joint of the user, such that the device is actually effective in breaking up scarred or injured tissue. Additionally or alternatively, the joint manipulation device may need to be operated for at least a certain period of time in order for the device to be effective. For example, the joint manipulation device may need to be operated by the user to apply a force for at least a predetermined period of time (e.g., one minute, five minutes, thirty minutes, etc.) during any exercise or stretching operation. Similarly, the monitoring entity (or a third-party entity such as a healthcare entity or insurance entity) may require or request that the user operates the joint manipulation device in timed intervals of stretching the joint and resting the joint.

Therefore, the joint manipulation device may be part of a system configured to measure each of these aspects of the user's operation of the joint manipulation device. As such, one or more force sensors may be placed in an area where the joint manipulation device engages a limb of the user, such that the force sensor(s) may measure the amount of force being exerted upon the limb and/or joint of the user. This measurement can be compared to a threshold force or pressure to determine if enough force is being exerted by the joint manipulation device to qualify as a compliant use of the device by the user. Additionally or alternatively, pressure sensors can tap into a hydraulic line of the joint manipulation device that is associated with moving the limb engaging members of the joint manipulation device. These pressure sensors can measure pressure changes in the hydraulic line to determine an amount of force being exerted by the device and/or felt by the limb and/or joint of the user. For example, in some embodiments, one or more pressure sensors comprise air pressure sensors that are configured to measure air pressure and/or changes in air pressure within a hydraulic line of the joint manipulation device.

Once the system determines that the user is operating the device in compliance with provided instructions or requirements, then the system can provide an indication or notification to the user that the user is in currently in compliance with the proper operation of the device. This indication can be in the form of an audible alert (e.g., a beep, multiple beeps, a voice command, etc.), a visual alert (e.g., an LED light color, an LED light flash or blink, a visual notification on a display of a computing device, etc.), a physical alert (e.g., a vibratory alert), and the like, that informs the user of the compliant status. If the amount of force measured by the system falls below the threshold, then the system can send another, possibly different, alert to the user. Additionally, once the system determines that the user has operated the joint manipulation device in compliance for an appropriate amount of time, the system can transmit another indication to the user that the user has completed one iteration of compliant operation of the device.

For example, in some embodiments, the monitoring entity may require or recommend that the user operates the joint manipulation device for 10 minutes at a time, followed by 10 minutes of rest, and then 10 more minutes of stretching. Additionally, the monitoring entity may require or request that the user conduct such a stretching regiment 3 times during the day, for a total of 60 minutes of stretching per day. Of course, these times are merely examples of the duration of stretching, the duration of rest, and the requested number of repetitions of the regiment over a period of time, and any combination may be utilized by the embodiments described herein. In such embodiments, the system may provide different indicators for each stage of the stretch. For example, a first audible alert (e.g., a single beep) may come on when the user first engages the joint manipulation device in a compliant way, a second audible alert (e.g., two beeps) may inform the user that the user has stretched for the recommended time (e.g., 10 minutes, etc.). After the rest period has concluded, the system may emit a third audible alarm (e.g., three beeps) to inform the user that the user should begin stretching the joint again. As such, once the user re-engages the joint manipulation device in a compliant manner, the first audible alert (e.g. a single beep) can inform the user that the user is back in compliance. Of course, any combination of alerts may be used, including no alerts, during the user's operation of the joint manipulation device.

Furthermore, while the device is being operated, certain information and data can be measured and extracted from the device by one or more sensors in a sensor assembly. In particular, the system may measure pressure, or force, being exerted by the joint manipulation device upon a joint and/or limb of a user, a duration of time that the device is under appropriate pressure, and progress of the patient in improving the user's range of motion for a joint. As such, the joint manipulation device system can measure data comprising force data, joint angle(s) data, time duration data, position data, and the like. As the data is measured, it can be recorded within device computing components operatively coupled to the joint manipulation device. The device computing components may then transmit aggregated user compliance data and device usage data to one or more devices or systems associated with the joint manipulation device. In some embodiments, this data is transmitted to the one or more devices or systems associated with the joint manipulation device in real time or in near real time, as the data is collected by the joint manipulation device system.

The compliance and device usage data can be transmitted to a mobile device or other computing device associated with the user, such that the mobile or computing device(s) of the user can aggregate and/or display the user's compliance with proper operation of the joint manipulation device as well as the user's progress in improving the range of motion of the user's injured joint. For example, the joint manipulation device may transmit its recorded information to a mobile application on a mobile device of the user, to allow the user to continually keep track of the user's progress and to let the user know whether the user is in compliance with the intended or instructed use of the joint manipulation device.

As used herein, the term "range of motion" generally refers to the available degrees of rotation that a joint (e.g., a knee joint, an elbow joint, a wrist joint, a shoulder joint, a foot joint, etc.) is capable of achieving. Additionally, the range of motion may be considered as a minimum and a maximum degree of rotation for the joint of the user, as measured by one or more sensors of the joint manipulation device system.

Similarly, the compliance and/or device usage data can be transmitted to a monitoring system associated with a monitoring entity that is providing the joint manipulation device. The monitoring system can track a user's compliance with the monitoring entity's product to ensure that the device is being used properly. Additionally, the monitoring entity may need to provide compliance and/or effectiveness data associated with one or more users' operation of one or more joint manipulation devices to an insurance organization or a regulatory body. The compliance and/or effectiveness data may be especially important in worker's compensation incidents, where compliance, recovery time, and progress are especially important to insurers. This data may be required to maintain payments from an insurance company to the monitoring entity, where the payments are insurance payments associated with a user's insurance policy. In some cases, these insurance payments will stop if the monitoring entity cannot prove that either (1) the user is still using the joint manipulation device, or (2) the joint manipulation device is not effective in improving the user's range of motion and/or recovery from a surgery. Without the invention described herein, the monitoring entity may rely on agents of the monitoring entity calling, visiting, or otherwise keeping track of a user and/or a user's medical provider to try to obtain proof that the user is still using the joint manipulation device and that the joint manipulation device is actually improving the user's range of motion in an injured joint.

Instead, the system embodiments described herein allow for reliable compliance and usage data to be recorded by the joint manipulation device system and transmitted directly to the monitoring entity system and/or an insurance agency system, thereby bypassing timely and expensive processes of tracking down the user and/or the user's medical provider for possibly incorrect information.

Furthermore, the effectiveness data of multiple users may be automatically received and compiled by a monitoring system (or a third party system) and aggregated based on certain metrics to form the basis of an overall effectiveness study in how the joint manipulation device is best utilized. In such embodiments, the monitoring entity, or whichever entity is performing the study, can exclude effectiveness data from exercise regimens that did not conform to the compliance standards set by the monitoring entity. This allows for a more accurate representation of the effectiveness of the joint manipulation device, while excluding outlier data that is not associated with compliant operation of the joint manipulation device.

FIG. 1 provides a block diagram illustrating a system and environment 100, in accordance with an embodiment of the invention. As illustrated in FIG. 1, the environment 100 includes a joint manipulating device system 200 comprising a joint manipulating device 202 with a limb engaging member 204, a force sensor 206 operatively coupled with the limb engaging member 204, a joint manipulation assembly 210, a sensor assembly 208, an indicator 212, and device computing components 214. The environment 100 also includes a user 110, a mobile device 300 associated with the user 110, a computing device 400 associated with the user 110, a monitoring system 500, and third party systems 600.

While a knee exerciser (e.g., a "knee flexionater") is illustrated as the joint manipulation device 202 in FIG. 1, any type of joint manipulation device 202 may be used in the system environment 100 to provide forces to one or more limbs or a joint of a user 110 designed to rehabilitate and/or improve the range of motion for that joint. Several other examples of joint manipulation devices 202 are provided in FIGS. 2A and 2G-K, but of course other joint manipulation devices 202 are contemplated and could be utilized herein.

As used herein, a "mobile device" 300 is any mobile communication device, such as a cellular telecommunications device (i.e., a cell phone or mobile phone), personal digital assistant ("PDA"), a mobile Internet accessing device (e.g., a tablet computer, a laptop computer, and the like), or other mobile device. The computing device 400 may be any device that employs a processor and memory and con perform computing functions, such as a personal computer, a mobile device, and the like.

The mobile device 300 and the computing device 400 are configured to communicate over a network 150 with the monitoring system 500 and, in some cases, the joint manipulation device system 200 and/or third party systems 600. The joint manipulating device system 200, the mobile device 300, the computing device 400, and the monitoring system 500 are each described in greater detail below with reference to FIGS. 2A-5. The network 150 may include a local area network (LAN), a wide area network (WAN), and/or a global area network (GAN). The network 150 may provide for wireline, wireless, or a combination of wireline and wireless communication between devices in the network. In one embodiment, the network 150 includes the Internet. In one embodiment, the network 150 includes a wireless telephone network 152.

In general, the device computing components 214 of the joint manipulating device system 200 are configured to connect with the network 150 to transmit data and information associated with the joint manipulation device system 200 to the mobile device 300, the computing device 400, the monitoring system 500, and/or the third party systems 600. In some embodiments, the device computing components 214 transmit the data and information associated with the joint manipulation device system 200 in real time, or in near-real time as the data is collected. In some embodiments, at least a portion of the device computing components 214 normally operate in a low energy standby mode, but power up periodically to send out the collected data over the network 150. In some embodiments, the various sensors such as the force sensor 206 can directly transmit data over the network 150.

While a single joint manipulating device system 200, a single user 110, a single mobile device 300, a single computing device 400, and a single monitoring system 500 are illustrated in FIG. 1, it should be known that multiple joint manipulating device systems 200, mobile devices 300, computing devices 400, and/or monitoring systems 500 may be included in the environment 100. Furthermore, not every element illustrated in FIG. 1 may be utilized. For example, in some embodiments, the mobile device 300 and/or the computing device 400 may not be included, or one device may serve the function of multiple devices.

In some embodiments of the invention, the third party systems 600 are configured to be controlled and managed by one or more third party entities (not shown in FIG. 1) over the network 150. For example, a third party system 600 may be associated with a medical provider (e.g., a physician's office, a physical therapist organization, a surgeon's office, a hospital, and the like) that can communicate with the monitoring system 500, the joint manipulation device system 200, the mobile device 300, and/or the computing device 400 over the network 150. Likewise, the third party system 600 may be associated with an insurance organization or a regulatory agency that receives information regarding the joint manipulation device system 200 either directly from the joint manipulation device system 200 over the network 150 or from one or more of the mobile device 300, the computing device 400, and the monitoring system 500. Similarly, the third party system 600 may be associated with an academic institution, research institution, laboratory, or the like, that accumulates data from one or more joint manipulation device systems 200 to conduct studies associated with patient use of the joint manipulation device 202.

Of course in some embodiments, the third party system 600 is actually managed by the same entity (the monitoring entity) that is associated with the monitoring system 500. For example, a monitoring entity may manage and monitor the use of the joint manipulation device system 200 using the monitoring system 500, while also conducting a clinical trial or other research study using a third party system 600.

FIGS. 2A-2K illustrate some embodiments of the joint manipulation device system 200, including some possible embodiments of the joint manipulation device 202 and some possible sensor assembly 208 configurations, among other components of the joint manipulation device system 200.

FIG. 2A illustrates one example of a joint manipulating device system 200, complete with one example of a joint manipulating device 202: a knee extension assistor. The illustrated joint manipulating device 202 includes a limb engaging member 204 that comprises, in this particular embodiment, a foot engaging member. Of course, any other type of limb engaging member may be used, based on which joint in a body of a user 110 the joint manipulating device 110 is designed to exercise and/or stretch. For example, the limb engaging member 204 could be a thigh and/or a lower leg (e.g., shin, calves, etc.) brace strapped or otherwise engaged with the leg of a user 110, such that as a force is applied to the limb engaging member 204, at least a portion of the force is applied to the engaged portion of the limb of the user, causing the limb to rotate or otherwise move relative to its respective joint. In some embodiments, multiple limb engaging members 204 are utilized to engage one or more limbs or portions of limbs of a user 110.

As illustrated in FIG. 2A, the foot of a user is engaged by the limb engaging member 204, and the limb engaging member 204 is manipulated by the joint manipulation assembly 210. The joint manipulation assembly 210 is any assembly, device, lever, hydraulic arm, pulley system, ratchet system, resistive system, spring system, and the like, that is configured to apply some force upon the limb engaging member 204 of the joint manipulation device 202.

The joint manipulation assembly 210 illustrated in FIG. 2A is a lever-actioned linear hydraulic arm 216 configured to move limb engaging member 204 linearly along a rail 218 (or track) of the joint manipulation device 202. In some embodiments, the user 110 is seated in a stationary chair, with the foot of the user 110 being secured within and engaged by the limb engaging member 204. Therefore, as the joint manipulation assembly 210 causes the limb engaging member 204 to move, the knee joint of the user 110 is flexed as the foot of the user 110 is pushed toward the body of the user 110, and extended as the foot of the user 110 is pulled away from the body of the user 110.

In some embodiments, a force sensor 206 is operatively coupled to the limb engaging member 204, such that the force sensor 206 is configured to receive a force being applied between the limb engaging member 204 and the engaged limb of the user 110. In some embodiments, the force sensor 206 comprises a force switch or a pressure switch that is configured to operate in at least two states. In a first state, the force received by the force sensor 206 is below a predetermined threshold (e.g., predetermined by the user 100, by a monitoring entity, by the joint manipulation device system 200, and the like). In a second state, the force received by the force sensor 206 is at or above the predetermined threshold. In some embodiments, when the force received by the force sensor 206 increases to cause the force threshold to be met, the force sensor may transmit one or more control signals to the device computing components 214 (e.g., the electrical components of the system), to cause the device computing components 214 to turn on or to transform from a low energy resting state to an active, data acquisition and data transferring state. In some embodiments, the force sensor 206 is a button that is fully depressed once the predetermined threshold is met. In other embodiments, the device computing components 214 measures the force received at the force sensor 206 and determines when the force threshold has been met.

While two operating states have been described for the force sensor, it should be noted that one, two, three, four, or any number of operating states can be used by the force sensor 206. These operating states can be based on one or more force thresholds, one or more timing thresholds (e.g., a force is applied for a certain period of time), a combination of force and timing thresholds, and the like.

In some embodiments, an indicator 212 is included in the joint manipulation device system 200. As illustrated in FIG. 2A, the indicator 212 may be an LED embedded within, or positioned on top of a handle of the joint manipulation device 202. FIG. 2C illustrates a closer look at an example of how an LED indicator 212 can be operatively coupled to a handle of the device. Of course, the indicator 212 can be positioned in any location on the joint manipulation device 202 that allows the user 110 to see, hear, or otherwise become aware of notices, warnings, encouragement, and the like. In some embodiments, the indicator 212 is a speaker or other audible device configured to emit a noise and/or a vibration to the user 110.

The indicator 212 may, in some embodiments, can be located on a display associated with the joint manipulation device 202. For example, the device computing components 214 may include a display that is configured to provide one or more indications to the user 110 before, during, and/or after the user's operation of the joint manipulation device. The indicator 212 may also be part of a mobile or computing device like the mobile device 300 and/or the computing device 400 illustrated in FIG. 1.

In some embodiments, the indicator 212 is connected to the pressure sensor 206 in such a manner that the indicator 212 provides one or more notifications or indications of the state of the pressure sensor 206. For example, the indicator 212 may emit a green light when a first pressure threshold has been met at pressure sensor 206, where the green light indicates that the user 110 is operating the joint manipulation device 202 in compliance with instructions or accepted operating instructions for the joint manipulation device. For example, in some embodiments, a monitoring entity (e.g., an entity associated with the monitoring system 500) may set the exercise goal of applying a pressure of at least 50 psi to the foot of the user 110. Therefore, the pressure threshold for the pressure sensor 206 on the limb engaging member 204 is set at 50 psi. Once the user 110 has cranked the lever associated with the joint manipulation assembly to push against the foot of the user 110 with a force of at least 50 psi, then the green light is emitted from the LED indicator 212, letting the user 110 know that an appropriate amount of force is being applied to the limb (and therefore the joint) of the user 110 to be in compliance with the exercise goals.

The monitoring entity may permit the force to dip at least a certain amount below the threshold pressure level (e.g., 50 psi) for a predetermined period of time (e.g., ten seconds, thirty seconds, one minute, etc.), and still consider the user's 110 operation of the joint manipulation device 202 to be in compliance. Therefore, the indicator 212 may change to a different color (e.g., red) when the force received by the force sensor 206 is below the force threshold for the predetermined period of time. Of course, the indicator 212 may also indicate that the user 110 is close to no longer being in compliance with the operating guidelines of the joint manipulation device 202. For example, the indicator 212 may display a different color light (e.g., a yellow light), flash, turn off, or the like, to indicate that the force being applied to the limb of the user 110 has dipped below the force threshold, but not for the predetermined period of time. This would allow a user to adjust the force manipulation assembly 210 to increase the force applied by the limb engaging member 204 to meet the compliance requirements.

Additionally or alternatively, the indicator 212 may comprise a speaker or other audible or vibratory device that operates similarly to the LED indicator 212 shown in FIG. 2C. For example, an audible indicator 212 may be operatively coupled to the joint manipulation device 202 in any position that allows the user 110 to hear the audible emissions from the indicator 212. For example, the audible indicator 212 may be operatively coupled to, or be a component of, the device computing components 214, which may or may not be operatively coupled to at least a portion of the joint manipulation device 202. Similar to the LED version of the indicator 212, an audible indicator 212 may emit beeps, tones, commands, voice messages, music, or other sound or vibration that can be received by the user 110. The emitted audible signal (e.g., beep, voice command, etc.) may vary based on signals from the force sensor 206, which are dependent on the received force from the engaged limb of the user 110 at the limb engaging member 204.

In some embodiments, the indicator 212 may emit an audible signal of a first type (e.g., a single beep, multiple beeps, a voice message, etc.) in response to the force measured by the force sensor 206 meeting and/or exceeding the force threshold. If the force measured or received by the force sensor 206 drops below the first threshold, the indicator 212 may respond by emitting an audible signal of a second type (e.g., a constant tone, two beeps, a voice message, etc.) to let the user 110 know that the user 110 is not using the joint manipulation device 202 as instructed or advised for best results. Furthermore, as with the LED version of the indicator 212, the audible device indicator 212 may emit an audible signal of a third type (e.g., three beeps, a long constant beep, a voice message, and the like) in response to the force received by the force sensor 206 has remained below the threshold force for more than a predetermined period of time, thereby informing the user 110 that the user's 110 operation of the joint manipulation device 202 was not proper and that the user 110 should restart the exercise or stretching set.

In some embodiments, instead of (or in addition to) audible signals, the indicator 212 may emit a vibration that is configured to be felt by at least a portion of the user 110. In some such embodiments, the indicator 212 comprises a vibratory device. The vibratory device may be operatively coupled to a portion of the joint manipulation device 202 (e.g., a chair, a handle, a brace, etc.). Additionally or alternatively, the vibratory device may be a component of a mobile or other electronic device (e.g., a mobile device like mobile device 300 or a computing device like computing device 400, etc.), such that the vibratory device is hand-held or is configured to engage a portion of the user 110 and transmit vibratory signals to the user 110 as it receives instructions to do so from the joint manipulation device system 200.

The joint manipulation device system 200 may also include a sensor assembly 208. The at least a portion of the sensor assembly 208 may be operatively coupled to the joint manipulation device 202. Additionally or alternatively, at least a portion of the sensor assembly 208 is positioned near the joint manipulation device such that sensors from the sensor assembly 208 are configured to take measurements or readings associated with the operation of the joint manipulation device 202 by the user 110.

In some embodiments, and as shown in FIG. 2A, at least a portion of the sensor assembly 208 is operatively or directly coupled to a portion of the joint manipulation assembly 210. For example, one or more force or pressure sensors (e.g., force switches, force transducers, pressure switches, pressure transducers, etc.) may be operatively coupled to a hydraulic line component of a joint manipulation assembly 210, where the hydraulic line component is operatively coupled to the limb engaging member 204 of the joint manipulation device 202. FIG. 2D illustrates one embodiment of a portion of a sensor assembly 208 comprising a pressure switch 220 and a pressure transducer 222 that are integrated with a hydraulic line 224 associated with a joint manipulation assembly 210. The hydraulic line 224 may also be operatively coupled to the limb engaging member 204, which is moveable along the rail 218 of the joint manipulation device 202, such that the joint manipulation assembly 210 causes the limb engaging member 204 to move along the rail 218 to engage and move a foot of a user 110. As such, when the foot of the user 110 engages the limb engaging member 204 with some degree of force, the hydraulic line 224 experiences a change in pressure that can be detected by, measured, and tracked by the sensor assembly 208. Furthermore, as the joint manipulation assembly 210 causes the limb engaging member 204 to slide along the rail 218, moving the foot of the user 110 (and therefore rotating the knee of the user 110), the pressure transducer 222 and/or the pressure switch 220 detect the changes in measured pressure of the hydraulic line 224, convert the pressure differences and/or pressure levels into electronic signals, and transmit the electronic signals to another component of the joint manipulation device system 200 (e.g., a different component of the sensor assembly 208, the computing device components 214, the indicator 212, etc.) or another system of the system environment 100 (e.g., the mobile device 300, the computing device 400, the monitoring system 500, and/or a third party system 600). The electronic signal received from the pressure transducer 222 and/or the pressure switch 220, can then be processed based on known algorithms and/or metrics associated with the positioning of the joint manipulation device 202, anthropomorphic measurements associated with the user 110, and the like, to determine a measured value (e.g., the force being exerted on the limb of the user 110, a positioning of the joint manipulation device 202, and angle of two or more components of the joint manipulation device 202, an angle of the joint of the user 110, etc.).

In some such embodiments, the pressure switch 220 may be the force sensor 206 of the joint manipulation device assembly 200. As such, the pressure switch 220 may be programmed or configured to automatically transmit a command signal configured to change a status (e.g., emit a beep, change a color of light emitted from an LED, etc.) of the indicator 204 (either directly or indirectly through the network 150) when the pressure switch 220 determines that the threshold pressure has been met. Similarly, the pressure switch 220 may be programmed to automatically transmit specific command signals configured to change a status of the indicator 204 based on multiple specific thresholds being met and/or not being met (e.g., the measured force falls below a first predetermined force threshold, the measured force meets or exceeds a second predetermined threshold associated with too much pressure being exerted, etc.).

The pressure switch 220 and the pressure transducer 222 in FIG. 2D tap into a hydraulic line 218 of the joint manipulation device 202, but any type of pressure or force switch and/or transducer may be used by the joint manipulation device system 200 to measure a force or pressure being exerted upon at least a portion of a limb or joint of a user 110. For example, in some embodiments of the invention, a pressure switch and/or a pressure transducer may measure air pressure and its changes within a pneumatic device of a joint manipulation assembly 210.

While a pressure switch 220 and a pressure transducer 222 are illustrated in FIG. 2D, it should be noted that any type of sensor may be utilized by the joint manipulation device system 200, and the sensor assembly 208 in particular. For example, linear potentiometers may be utilized to measure a distance of the limb engaging member 204 from a predetermined position. One example implementation of a linear potentiometer within a joint manipulation device system 200 is illustrated in FIGS. 2E-F. The linear potentiometer 226 may comprise a dial 228 and a line 230, where one end of the line 230 is wrapped (e.g., spooled) around the dial 228 at one end, and operatively coupled to the limb engaging member 204 at the other end of the line 230. Of course, the line 230 may be operatively coupled to any part of the joint manipulation device 202 such that as parts of the joint manipulation device 202 move to rotate or otherwise exercise the joint of the user 110, the linear potentiometer 226 measures a change in length of the line 230 extending from the dial 228 that is associated with the degree of rotation of the joint of the user 110.

For example, as shown in FIG. 2G, the user 110 may be seated in a stationary chair 232 (e.g., the chair 232 may be operatively coupled to a known location of the joint manipulation device 202) such that a buttocks of the user 110 is in a known position within the joint manipulation device system 200, while the foot of the user 110 is engaged by the limb engaging member 204. The linear potentiometer 226 of the joint manipulation device system 200 can measure a location of the limb engaging member 204 along the rail 218. This location measurement can be automatically transmitted to the device computing components 214 (or to a different system of the system environment 100 described herein), where the relative position of the buttocks of the user 110 is known or stored, such that the device computing components 214 can calculate or estimate an angle of the knee joint of the user 110 based on the measured location of the limb engaging member 204, the known buttocks location, and known or estimated anthropometric information associated with the leg of the user 110.

Therefore, the linear potentiometer 226, and particularly the dial 228 in some embodiments, may transmit measurement and/or command signals to the device computing components 214 and/or other systems of the system environment 100 that provide position and/or movement information for one or more portions (e.g., the limb engaging member 204, etc.) of the joint manipulation device 202.

FIGS. 2E and 2F further illustrate one embodiment of how the line 230 from the linear potentiometer 226 can be embedded within or positioned within one or more channels or grooves of a rail 218, such that the line 230 is protected from manipulation or damage from external elements.

Of course, any type of potentiometer or other resistor-based sensor may be utilized by the joint manipulation device system 200 and the sensor assembly 208 to measure distance and movement parameters associated with at least a portion of the joint manipulation device 202. For example, in some embodiments, a rotary potentiometer (not shown) may be operatively coupled to the joint manipulation device 202 at a location on or near the joint of the user 110 such that the rotary potentiometer measures degree of rotation between two limb portions on either side of the joint of the user 110. For example, the rotary potentiometer may be operatively coupled to (or extend across) a hinge of a knee or elbow brace of a joint manipulation device 202, such that the angle of the hinged brace, which is analogous to the angle of the joint of the user 110, can be measured by the rotary potentiometer.

In some embodiments (e.g., in shoulder range of motion devices), measurements of multiple degrees of rotation are desired. Therefore, in some embodiments of the invention, multiple rotary and/or linear potentiometers may be utilized by the joint manipulation device system 200 to track a joint's rotation and/or displacement along multiple axes.

Again, while a pressure switch 220, a pressure transistor 222, and a potentiometer 226 are illustrated and described in portions of this description, it should be noted that any type and/or combination of sensors may be used to comprise the sensor assembly 208 of the joint manipulation device system 200. Examples of other types of sensors that may be used within the sensor assembly 208 include, but are not limited to laser sensors, ultrasonic sensors, infrared sensors, optical sensors, accelerometers, and the like, that are operatively coupled to, or are otherwise configured to detect and/or measure, locations or positions of one or more portions of the joint manipulation device 202. Furthermore, any type of angle sensor may be implemented to directly measure an angle of a joint of the user 110, including, but not limited to, linear potentiometers, rotary potentiometers, and the like.

For example, to measure a distance of one or more components of the joint manipulation device 202, a laser sensor may take periodic or continuous measurements of a distance of the limb engaging member 204, relative to a known position of the joint manipulation device 202.

In some embodiments, the sensor assembly 208 includes one or more force sensors that measure a force exerted by one or more limb engaging members 204 against one or more portions of one or more limbs of a user 110. In such embodiments, the force sensors provide information associated with the force being exerted against a limb of the user 110 to stretch and/or rotate the joint of the user 110.

The sensor assembly 208 may comprise one or more accelerometer sensors operatively coupled to a portion of the joint manipulation device 202 such that movement, acceleration, rotation, orientation, and the like, of the portion of the joint manipulation device 202 can be measured. For example, an accelerometer sensor may measure the acceleration of a lower portion of a leg of a user 110 as it extends or flexes during the operation of the joint manipulation device 202 by the user 110. This acceleration and/or orientation information can be measured by the accelerometer sensor of the sensor assembly 208 and transmitted or stored for future analysis by the joint manipulation device system 200.

Other types of sensors can make up or be utilized by the sensor assembly 208 including, but not limited to, heart rate monitors, temperature sensors, scales, and the like. The sensor assembly may also comprise one or more clocks or other timing devices that operate in conjunction with, or separately from, one or more of the sensors. The one or more clocks may be triggered to begin timing or record start and stop times, based on input from one or more of the sensors in the sensor assembly 208. For example, when a pressure switch determines that the threshold pressure has been met, it may transmit a command signal to cause a clock to record the start time and/or begin timing for the duration that the measured pressure remains above the threshold pressure.

The sensors of the sensor assembly 208 may communicate their measurements or readings to one or more other components of the joint manipulation device system 200 (e.g., the sensor assembly 208, device computing components 214, etc.) and/or the system environment 100 (e.g., mobile device 300, computing device 400, monitoring system 500, and/or a third party system 600) over a wired connection and/or over a wireless network connection (e.g., the network 150). The sensor readings may be transmitted wirelessly in many ways including, but not limited to, near field communication (NFC), Bluetooth communication, Zig-Bee communication, radio frequency identification (RFID) communication, wireless local area network (WLAN) (e.g., Wi-Fi), mobile phone communication, and the like.

Of course, in some embodiments, the measurements and/or readings of the sensors in the sensor assembly 208 are communicated to the device computing components 214, which then transmits the measurements and/or readings to one or more systems (e.g., the mobile device 300, the computing device 400, the monitoring system 500, and/or one or more third party systems 600).

The device computing components 214 may be operatively coupled to the joint manipulation device 202, as shown in FIG. 2A, where the device computing components 214 are stored beneath a the rail 218 and protected from some of the moving components of the joint manipulation device 202. Of course, the device computing components 214 may be positioned anywhere on the joint manipulation device 202, and may be broken into multiple sets of components along the joint manipulation device 202. In some embodiments, the device computing components 214 may be positioned externally from the joint manipulation device 202, such as on an external server, a mobile device, a computing device, and the like. The device computing components 214 may be in network communication with the sensor assembly 208 and/or other components of the joint manipulation device 202, to receive signals associated with the operation of the joint manipulation device 202 by the user 110 and to transmit information and data associated with the operation of the joint manipulation device 202 to one or more systems (e.g., the mobile device 300, the computing device 400, the monitoring system 500, and/or one or more third party systems 600).

FIG. 2B provides a block diagram illustrating a joint manipulating device system's 200 device computing components 214 of FIGS. 1 and 2A in more detail, in accordance with embodiments of the invention. In one embodiment of the invention, the device computing components 214 may be any type of computing device, mobile computing device, or any other computing device such as a portable digital assistants (PDAs), pagers, mobile televisions, gaming devices, laptop computers, cameras, video recorders, audio/video player, radio, GPS devices, or any combination of the aforementioned.

Some embodiments of the device computing components 214 include a processor 111 communicably coupled to such devices as a memory 120, user output devices 136, user input devices 140, a network interface 160, a power source 115, a clock or other timer 150, a camera 180, and a positioning system device 175. The processor 111, and other processors described herein, generally includes circuitry for implementing communication and/or logic functions of the device computing components 214. For example, the processor 111 may include a digital signal processor device, a microprocessor device, and various analog to digital converters, digital to analog converters, and/or other support circuits. Control and signal processing functions of the device computing components 214 are allocated between these devices according to their respective capabilities. The processor 111 thus may also include the functionality to encode and interleave messages and data prior to modulation and transmission. The processor 111 can additionally include an internal data modem. Further, the processor 111 may include functionality to operate one or more software programs, which may be stored in the memory 120. For example, the processor 111 may be capable of operating a connectivity program, such as a web browser application 122. The web browser application 122 may then allow the device computing components 214 to transmit and receive web content, such as, for example, location-based content and/or other web page content, according to a Wireless Application Protocol (WAP), Hypertext Transfer Protocol (HTTP), and/or the like.

The processor 111 is configured to use the network interface 160 to communicate with one or more other devices on the network 150. In this regard, the network interface 160 includes an antenna 176 operatively coupled to a transmitter 174 and a receiver 172 (together a "transceiver"). The processor 111 is configured to provide signals to and receive signals from the transmitter 174 and receiver 172, respectively. The signals may include signaling information in accordance with the air interface standard of the applicable cellular system of the wireless telephone network 152. In this regard, the device computing components 214 may be configured to operate with one or more air interface standards, communication protocols, modulation types, and access types. By way of illustration, the device computing components 214 may be configured to operate in accordance with any of a number of first, second, third, and/or fourth-generation communication protocols and/or the like. For example, the device computing components 214 may be configured to operate in accordance with second-generation (2G) wireless communication protocols IS-136 (time division multiple access (TDMA)), GSM (global system for mobile communication), and/or IS-95 (code division multiple access (CDMA)), or with third-generation (3G) wireless communication protocols, such as Universal Mobile Telecommunications System (UMTS), CDMA2000, wideband CDMA (WCDMA) and/or time division-synchronous CDMA (TD-SCDMA), with fourth-generation (4G) wireless communication protocols, with LTE protocols, with 1GPP protocols and/or the like. Future wireless and wired communication protocols are also envisioned such as fifth-generation wireless communication protocols. The device computing components 214 may also be configured to operate in accordance with non-cellular communication mechanisms, such as via a wireless local area network (WLAN), or other communication/data networks.

The network interface 160 may also include a device computing component interface 170. The device computing component interface 170 may include software, such as encryption software, and hardware, such as a modem, for communicating information to and/or from one or more devices on a network 150 and connected with or that are part of the monitoring system 500. For example, the device computing components 214 may be configured so that it can be used as an interface for interacting with the joint manipulation device system 200 to receive information regarding the operation of the joint manipulation device 202 and/or to provide notes or instructions to the joint manipulation device system 200. Similarly, the device computing component interface 170 may be configured so that it can transmit information aggregated or derived from the device computing component (e.g., information and data associated with the operation of the joint manipulation device 202) to the monitoring system 500 or a third party system 600.

The device computing components 214 may also comprise one or more sensor assembly inputs 141. The sensor assembly inputs may be any type of communication interface with the one or more sensors associated with the joint manipulation device system 200, and may comprise a direct or wired connection to a sensor, a wireless connection to a sensor, and the like. As such, the device computing components 214 may include short range communication devices 142. The short range communication devices 142 may comprise near field communication (NFC) devices, Bluetooth communication devices, radio-frequency identification (RFID) communication devices, ZigBee communication devices, and the like.

As described above, the device computing components 214 has a user interface that is, like other user interfaces described herein, made up of user output devices 136 and/or user input devices 140. The user output devices 136 include a display 130 (e.g., a liquid crystal display, LED display, or the like) and a speaker 132 or other audio device, which are operatively coupled to the processor 111. In some embodiments, the user output devices 136 includes one or more vibratory devices 134 that vibrate or otherwise move a portion of the joint manipulation device 202, or a mobile device in response to certain command signals. In some embodiments of the invention, one or more of the user output devices 136, including the display 130, the speaker 132, and the vibratory device 134, may act as the indicator 212 of the joint manipulation device system 200.

The user input devices 140, which allow the device computing components 214 to receive data from a user such as the user 110, may include any of a number of devices allowing the device computing components 214 to receive data from the user 110 such as a keypad, keyboard, touchscreen, touchpad, microphone, mouse, joystick, other pointer device, button, soft key, and/or other input device(s). The user interface may also include a camera 180, such as a digital camera.

The device computing components 214 may also include a positioning system device 175 that is configured to be used by a positioning system to determine a location of the device computing components 214. For example, the positioning system device 175 may include a GPS transceiver. In some embodiments, the positioning system device 175 is at least partially made up of the antenna 176, transmitter 174, and receiver 172 described above. For example, in one embodiment, triangulation of cellular signals may be used to identify the approximate location of the device computing components 214. In other embodiments, the positioning system device 175 includes a proximity sensor or transmitter, such as an RFID tag, that can sense or be sensed by devices known to be located proximate the joint manipulation device system 200 or other location to determine that the device computing components 214 is located proximate these known devices.

The device computing components 214 further includes a power source 115, such as a battery, for powering various circuits and other devices that are used to operate the device computing components 214. Embodiments of the device computing components 214 may also include a clock or other timer 155 configured to determine and, in some cases, communicate actual or relative time to the processor 111 or one or more other devices. For example, in some embodiments, the clock 155 of the device computing components 214 is configured to provide timing information associated with the operation of the joint manipulation device system 200 by the user 110 (e.g., timing of exercises, duration of exercises, and the like).

The device computing components 214 also includes a memory 120 operatively coupled to the processor 111. As used herein, memory includes any computer readable medium (as defined herein below) configured to store data, code, or other information. The memory 120 may include volatile memory, such as volatile Random Access Memory (RAM) including a cache area for the temporary storage of data. The memory 120 may also include non-volatile memory, which can be embedded and/or may be removable. The non-volatile memory can additionally or alternatively include an electrically erasable programmable read-only memory (EEPROM), flash memory or the like.

The memory 120 can store any of a number of applications which comprise computer-executable instructions/code executed by the processor 111 to implement the functions of the device computing components 214 and/or one or more of the process/method steps described herein. For example, the memory 120 may include such applications as a conventional web browser application 122 and/or a joint manipulation device application 121. These applications also typically provide a graphical user interface (GUI) on the display 130 that allows the user 110 to communicate with the device computing components 214, the monitoring system 500, and/or other devices or systems (e.g., the joint manipulation device system 200, the computing device 400, and the third party systems 600). In one embodiment of the invention, when the user 110 is provided with a joint manipulation device system 200 that is associated with a software produce, the user may download, is assigned, or otherwise obtains the joint manipulation device application 121 from the monitoring entity 500, or from a distinct application server. In other embodiments, the user 110 interacts with the monitoring system 500 via the web browser application 122 in addition to, or instead of, the joint manipulation device application 121.

The memory 120 can also store any of a number of pieces of information, and data, used by the device computing components 214 and the applications and devices that make up the device computing components 214 or are in communication with the device computing components 214 to implement the functions of the device computing components 214 and/or the other systems described herein. For example, the memory 120 may include such data as user authentication information, anthropometric measurements of the user 110, target range of motion data associated with the user 110 and the associated joint manipulation device system 200, and the like.

FIG. 2G illustrates one embodiment of a joint manipulation device 202, particularly a knee extension and/or flexing apparatus, in accordance with embodiments of the present invention. In some embodiments, the joint manipulation device 202 comprises the apparatus for enabling the movement of human limbs and method for using same, as described in detail in U.S. Pat. No. 6,872,186. In some such embodiments, the user 110 may control the movement of the limb engaging member 204 (and thereby the movement of the foot 234 of the user 110) by operating a handle component of the joint manipulation assembly 210. The joint manipulation assembly may be a hydraulic system that includes the pressure switch 220 and the pressure transducer 224 operatively coupled to the hydraulic line 224, as described in FIGS. 2D-2F.

As such, when the user 110 manipulates the handle 236 of the joint manipulation assembly 210, the hydraulic line 224 causes the limb engaging member 204, which is engaged with the foot 234 of the user 110, to slide along the rail 218. Because the user 110 is seated in a stationary chair 232, the knee joint 238 of the user 110 is extended or flexed as the limb engaging member 204 is moved along the rail 218. The pressure switch 220 and/or the pressure transducer 224 may measure, record, and/or transmit signals associated with the pressure and/or positioning of the limb engaging member 204, relative to the rest of the joint manipulation device 202. These measurements may be indicative of the status or general operation of the joint manipulation device 202, as it relates to the stretching or exercising of the knee joint 238 of the user 110. A linear potentiometer like the linear potentiometer 226 described in relation to FIGS. 2E and 2F, may be operatively coupled to the joint manipulation device 202, to measure and transmit positioning or movement information associated with the limb engaging member 204 along the rail 218 of the joint manipulation device 202.

As described above, the sensor assembly 208 may receive the pressure, force, distance, angle, timing, and other information measured by the sensors in the joint manipulation device system 200. This data may be transmitted to the device computing components 214 and/or a mobile or computing device associated with the joint manipulation device system 200. The device computing components 214 may then aggregate usage data associated with the operation of the joint manipulation device 202 by the user 110, determine whether the user 110 is operating the joint manipulation device 202 in compliance with standards or instructions set by the monitoring system 500 (or another system or entity), and provide feedback to the user 110 and/or the monitoring system 500 through a transmission of signals and/or data. For example, the device computing components may cause a speaker (e.g., the speaker 132 illustrated in FIG. 2B) to emit a beep, tone, voice command, or other audible alert to the user in direct response to determining that the user 110 (a) is in compliance with the suggested operation of the joint manipulation device 202, (b) is not in compliance with the suggested operation of the joint manipulation device 202, (c) has operated the joint manipulation device 202 for an appropriate amount of time, (d) needs to increase the force being applied to the foot 234 of the user 110 to remain in compliance with the suggested operation of the joint manipulation device 202, and the like.

In some embodiments, once the monitoring system 500 receives the information from the sensors and aggregates or otherwise analyzes the usage data associated with the user's 110 operation of the joint manipulation device 202, the monitoring system 500 may determine that one or more functions or features of the joint manipulation device system 200 needs to be adjusted. For example, the monitoring system 500 may determine that the user 110 has utilized the joint manipulation device 202 to cause the joint of the user 110 to gain a full range of motion (or close to a full range of motion), and therefore determines that a resistance of the joint manipulation device 202 should be increased to provide a better stretching feature for the user. Therefore, the monitoring system 500 may cause the joint manipulation device 202 to increase the resistance a specified amount. In some embodiments, the monitoring system 500 and/or the joint manipulation device system 200 may provide a request for adjusting the joint manipulation device 202 to the user 110 at a display of the joint manipulation device system 200 and/or the mobile device 300.

In this way, the user 110 may accept or deny the request to adjust features of the joint manipulation device 202, and therefore has full control of the joint manipulation device 202. Other examples of functions or features that may be adjusted by the monitoring system 500 include, but are not limited to, range of motion degrees that the joint manipulation device 202 may exercise, exercise duration requirements, one or more positioning angles for the joint of the user within the joint manipulation device, and the like. In some embodiments, a doctor, physician, or other medical professional has access to the transmitted usage data from the joint manipulation device system 200, and is able to input one or more of the adjustments to the joint manipulation device 202 based on the received usage data. For example, a physician may receive usage data of the joint manipulation device 202, determine that the force threshold should be increased by a certain amount, and then input this certain amount into an interface of the monitoring system, which can remotely adjust the force threshold associated with the user 110 and the joint manipulation device 202.

Therefore, in some embodiments, a medical professional may set an initial threshold associated with the user's 110 compliance with the operation of the joint manipulation device 202. Examples of what the threshold may comprise include, but are not limited to, a minimum force being exerted by the joint manipulation device 202 upon a limb of the user 110 to be in compliance, a maximum force being exerted by the joint manipulation device 202 upon a limb of the user 110 to be in compliance, a minimum angle of the joint of the user's 110 limbs to be in compliance, a maximum angle of the joint of the user's 110 limb to be in compliance, a minimum time of exercise to be in compliance, a maximum time of exercise to be in compliance, a minimum frequency of stretching a joint of the user 110 to be in compliance, and/or a maximum frequency of stretching a joint of the user 110 to be in compliance. Assuming, for illustrative purposes, that the medical professional has set a minimum force threshold for a sensor configured to measure a force exerted upon a limb of the user 110, then this threshold may be input or otherwise stored in a database of the joint manipulation device system 200 and/or the monitoring system 500. The monitoring system 500 can then track usage data and compliance data of the joint manipulation device 202, and provide a report of the monitored data back to the medical professional. The medical professional may then determine that the user 110 is currently unable to meet the minimum pressure threshold when exercising the joint. Therefore, the system may provide an input interface to the medical professional that allows the medical professional to adjust the force threshold to a value that is appropriate for the stage of the user's 110 recovery. In some embodiments, this new or adjusted threshold input is automatically updated into the system. In other embodiments, the adjusted threshold input is first presented to the user 110, providing the user 110 the chance to consent to the changes, request additional information from the medical professional, manually perform the changes, and/or deny the changes, thereby remaining in control of the operation of the joint manipulation device 202.

As such, the monitoring system 500 and/or a medical professional may transmit a notification to the user 110 (e.g., through a display of the joint manipulation device system 200, the mobile device 300, and/or the computing device 400), where the notification comprises instructions or a request for the user 110 to manually adjust the joint manipulation device based on the instructions. In such embodiments, the monitoring system 500 may comprise or otherwise be associated with one or more computing devices or mobile devices associated with the medical professionals.

Additionally or alternatively, the device computing components 214 may automatically or periodically transmit the usage data and information about the operation of the joint manipulation device 202 by the user 110 to the monitoring system 500. For example, a monitoring entity associated with the monitoring system 500 may desire information associated with the user's 110 operation of the joint manipulation device 202 to determine if the user 110 is operating the joint manipulation device 202 in compliance with instructions given to the user or general standards of the joint manipulation device 202. This data may be important to the monitoring entity because it allows the monitoring entity to track the progress of a user 110 in increasing a range of motion for one or more joints of the user 110, which may be the intended use of the joint manipulation device 202. By testing and validating the monitoring entity's product (i.e., the joint manipulation device 202), the monitoring entity can ensure and prove that the provided guidelines of use are effective in increasing a user's 110 range of motion for joints. The progress documented by the monitoring system can be used by clinicians to make treatment decisions such as requesting the patient come in for an office visit, or discontinuing use of the device due to sufficient recovery or lack of progress.

Furthermore, the monitoring entity may be required to report usage and effectiveness data to one or more companies or agencies. For example, the monitoring entity may be required to provide reports to one or more insurance companies on the effectiveness of a joint manipulation device 202 for each user 110 using a joint manipulation device 202. As such, the monitoring entity system 500 may receive compliance and efficiency data associated with a user's 110 operation of the joint manipulation device 202, and automatically, periodically, or manually transmit the compliance and/or efficiency information to an appropriate insurance agency. In some embodiments, the device computing components 214 of the joint manipulation device system 200 may transmit the compliance information (either in a raw form, or aggregated or formatted into a report) to one or more third party systems 600 (e.g., an insurance company).

In some embodiments, a monitoring entity may desire efficiency information about the joint manipulation device 202 for multiple users 110 (e.g., for a study). As such, the monitoring system 500 may receive device usage, compliance, and efficiency information for multiple joint manipulation devices 202 associated with a plurality of users 110. The data may be transferred directly to the monitoring system 500 from each of the joint manipulation devices 202 (e.g., from the device computing components 214, etc.). This bypasses requiring each user 110, agents of the monitoring entity, and/or medical professionals to record usage or efficiency information and provide such information to the monitoring entity. The monitoring entity can also filter out exercises by users 110 that were not in compliance with the instructions for operation of the joint manipulation devices (e.g., the force threshold was not met for a predetermined time of exercise). In this way, the monitoring entity can monitor the effectiveness of the joint manipulation devices 202 based on actual, proper uses of each joint manipulation device 202 without requiring a professional to watch over each user 110 during the stretches or exercises.

FIG. 2H illustrates another embodiment of the joint manipulation device 200, associated with exercising the shoulder joint and/or elbow joint of a user 110. In some embodiments, the joint manipulation device 202 described herein may be the shoulder extension control device described in U.S. Pat. No. 7,547,289. Many of the concepts described above, particularly with respect to FIG. 2G, are applicable in the joint manipulation device 202 of FIG. 2H, although the components may be positioned differently to exercise the appropriate joints 240, 242 of the user 110 and/or to measure the operation of the joint manipulation device 202 by the user 110 to determine whether the operation is compliant with instructions or suggestions provided to the user 110.

As shown in FIG. 2H, multiple limb engaging members 204a and 204b may be included in the joint manipulation device 202. The first limb engaging member 204a may engage at least a portion of the upper arm 246 of the user 110, while the second limb engaging member 204b may engage the forearm and/or hand 248 of the user 110. One or more force sensors 206a and 206b may be operatively coupled to the first limb engaging member 204a and the second limb engaging member 204b, respectively, to measure and/or track a force or pressure exerted upon the arm 246 and/or 248 of the user 110 over time.

The user 110 may operate the handle 236 of the joint manipulation assembly 210 to cause the first limb engaging member 204a and/or the second limb engaging member 204b to rotate about an axis at the shoulder joint 240 of the user 110, causing the shoulder joint 240 and/or the elbow joint 242 to rotate in one or more of the following motions: abduction, adduction, internal rotation, external rotation, flexion, and extension.

The first force sensor 206a and/or the second force sensor 206b may determine whether the user's 110 operation of the joint manipulation device 202 has engaged the first and/or second limb engaging members 204a and 204b sufficiently to meet compliance requirements, as described above. Because multiple directions of movement are possible with the joint manipulation device 202 setup illustrated in FIG. 2H, the force sensors 206a and 206b may be positioned at multiple points along the limb engaging member 204a and 204b, respectively, to measure forces associated with the limb 246 and 248 of the user 110 being engaged to rotate in any direction. For example, when measuring adduction of a shoulder joint 240, a force sensor 206a may be positioned on an upper part of the limb engaging member 204a (that faces downward, to receive the upper arm 246 of the user 110), such that the force sensor 206a may measure the force being exerted downward upon the upper arm 246 of the user 110, as the joint manipulation device 202 exercised the shoulder joint 240 into adduction. Likewise, when exercising the shoulder joint 240 in abduction, the joint manipulation device 220 is pushing upward on the upper arm 246 of the user 110, so the force sensor 206a may be positioned on a lower portion of the limb engaging member 204a (that faces upward, to receive a bottom portion of the upper arm 246 of the user 110), such that the force sensor 206a measures the force being exerted upward upon the upper arm 246 of the user 110.

As described above, a predetermined force threshold may be required for the operation of the joint manipulation device 202 by the user 110 to be considered in compliance. Therefore, the force sensors 206a and/or 206b may be configured to transmit command signals configured to cause the indicator 212 to notify the user 110 of the compliance status of the joint manipulation device over time. The indicator 212 illustrated in FIG. 2H comprises a speaker that is configured to emit one or more audible signals to the user 110 in response to receiving the command signals from the force sensors 206a and/or 206b, and/or other components of the joint manipulation device system 200 (e.g., the sensor assembly 208, the device computing components 214, etc.).

In some embodiments, the joint manipulation assembly 210 of the joint manipulation device 202 in FIG. 2H may comprise a hydraulic system that causes the limb engaging members 204a and/or 204b to rotate about the shoulder joint 240 and/or the elbow joint 242 of the user 110. A shoulder engaging member 244 may also be manipulated by the joint manipulation assembly 210 to aide in the rotation of the shoulder joint 240. The hydraulic joint manipulation assembly 210 may include a hydraulic line like the hydraulic line 224 illustrated in FIGS. 2D-2F. As such, the sensor assembly 208 may comprise one or more pressure switches like the pressure switch 220, and/or one or more pressure transducers like the pressure transducer 222 that are operatively coupled to a portion of the hydraulic line used in the manipulation of the limb engaging members 204a and 204b of the joint manipulation device 202. These pressure switches and/or pressure transducers may measure and/or track the pressure values and changes in pressure within the hydraulic line that are associated with movement of portions of the joint manipulation device 202 and/or the force(s) exerted by the upper arm 246 and/or the forearm 248 of the user 110 upon portions of the joint manipulation device 202. As described above, a pressure switch and/or a pressure transducer in a hydraulic line of the joint manipulation device 202 may operate as the pressure switch 206 described in more detail above. The measurements of the pressure switch and the pressure transducer may be converted into signals and transmitted to the device computing components 214 of the joint manipulation device system 200. As described above, while the device computing components 214 are illustrated as being operatively coupled to a specific portion of the joint manipulation device 202, it should be noted that the device computing components 214 may be operatively coupled to any portion of the joint manipulation device 202, or may be positioned externally from the joint manipulation device 202.

The sensor assembly 208 may also comprise one or more rotary potentiometers, operatively coupled to the joint manipulation device 202 at or about the shoulder joint 240 of the user 110, such that the rotary potentiometer(s) may measure angles and angular movement of the joint along one or more axes. Of course, any other type of sensor that can measure or deduce an angle of rotation for the shoulder joint 240 may be utilized in the sensor assembly 208.

FIG. 2I illustrates another non-limiting example embodiment of the joint manipulation device system 200, in accordance with embodiments of the invention. The joint manipulation device in FIG. 2I may be a knee joint 238 extension assisting device comprising an upper brace 250a, a lower brace 250b, one or more upper limb engaging members 204a, one or more lower limb engaging members 204b, and a joint manipulation assembly 210 configured to cause the knee joint 238 of the user 110 to extend when in operation. In some embodiments, the joint manipulation device 202 of FIG. 2I may be one or more embodiments of the device with therapeutic features described in U.S. patent application Ser. No. 13/838,308.

As shown in FIG. 2I, an upper limb force sensor 206a may be operatively coupled to the upper limb engaging member 204a underneath the upper leg of the user 110, such that a force between the upper limb engaging member 204a and the upper leg of the user 110 can be measured. Likewise, a lower limb force sensor 206b may be operatively coupled to the lower limb engaging member 204b underneath the lower leg of the user 110, such that a force between the lower limb engaging member 204b and the lower leg of the user 110 can be measured. These force or pressure measurements can be compared with one or more predetermined force or pressure thresholds, as described above, and information can be transmitted to the sensor assembly 208, the device computing components 214, or other systems (e.g., directly to a mobile device 300).

Additionally or alternatively, a sensor assembly 208 may be operatively coupled to the joint manipulation device 202 to measure one or more pressures or forces being exerted upon one or more portions of the leg of the user 110 about the knee joint 238, and/or to measure one or more angles of the knee joint 238 over time as the user 110 operates the joint manipulation device 202. For example, the user 110 may be able to tighten an extension assistor line 252 between two extended bridge members 254a and 254b, thereby causing the joint manipulation device 202 to urge the knee joint 238 of the user 110 into a more extended position. In some embodiments, the extension assistor line 252 may comprise a linear potentiometer line (or an additional, non-weight bearing linear potentiometer line may accompany the extension assistor line 252), such that the length of the extension assistor line 252 may be measured by the sensor assembly 208. The length of the extension assistor line 252 is indicative of the angle of the knee joint 238, so such information may be useful in determining a user's 110 operation of the joint manipulation device 202.

The sensor assembly 208 may measure the duration of such a stretch (e.g., how long a pressure threshold is met), an angular position of the knee joint 238 at any given point in time, a maximum (i.e., most extended) angle of the knee joint 238 over a certain period of time, and the like. In some embodiments, the measurements of the sensor assembly 208 may be transmitted to the device computing components 214.

In some embodiments, a joint manipulation device 202 may not comprise certain user interfaces or user display components. In such embodiments, and as described and illustrated in FIG. 2I, the sensor assembly 208 and/or the device computing components 214 may transmit data and information regarding the operation of the joint manipulation device 202 to a separate device like the mobile device 300. The mobile device 300 may then process the received signals from the sensor assembly and/or the device computing components 214, and perform any commands such as emitting an audible signal from a speaker 332 or displaying a light or message from one or more displays 330.

In some embodiments, the joint manipulation device 202 illustrated in FIG. 2I may comprise one or more inflatable bladders (not shown) positioned between the top of the upper leg of the user 110 and the upper limb engaging member 204a, and/or positioned between the top of the lower leg of the user 110 and the lower limb engaging member 204b. In such embodiments, the sensor assembly 208 may comprise one or more pressure sensors may be placed within each of the inflatable bladders and/or between the inflatable bladders and either the legs of the user 110 or between the inflatable bladders and the limb engaging members 204a and 204b. As such, these pressure sensors may detect and/or measure one or more pressure or force measurements associated with the inflatable bladders and the joint manipulation device system 200. Particularly, these pressure sensors may measure one or more forces exerted by the bladders upon one or more portions of the leg of the user 110 that are configured to cause the knee joint 238 of the leg of the user 110 to further stretch into an extended state, as the bladders are inflated. Additionally or alternatively, air pressure sensors may be placed within the inflatable bladder members to detect and measure values and changes in air pressure of the inflatable bladders as they are used in the operation of the joint manipulation device 202.

Similar to the knee extension assistor illustrated in FIG. 2I is one embodiment of an elbow flexion assistor version of the joint manipulation device 202, as illustrated in FIG. 2J. In some embodiments, the joint manipulation device 202 in FIG. 2J comprises one or more embodiments of the devices described in U.S. patent application Ser. No. 14/569,628. In some embodiments, the force switches 206a and 206b, if included, may be operatively coupled to upper portions of limb engaging members 204a and 204b, as illustrated in FIG. 2J, such that as the joint manipulation device 202 causes the joint manipulation device 202 to flex the elbow joint 242 of the user 110, the force switches 206a and/or 206b can measure a force exerted between at least a portion of the limb of the user 110 and the limb engaging members 204a and/or 204b.

The joint manipulation assembly may comprise a tensile member 256 operatively coupled to one or more bridges 254a and 254b, such that as the length of the tensile member 256 is shortened by the joint manipulation assembly (e.g., a rotary device operatively coupled to the tensile member), the one or more bridges 254a and 254b cause the limb engaging members 204a and 204b to push portions of the limb of the user 110 into extension substantially at portions where the pressure sensors 206a and 206b are positioned.

Additionally or alternatively, the system may comprise one or more sensor assemblies 208, each comprising one or more sensors to measure aspects of the joint manipulation device 202, and the user's 110 operation thereof. For example, one sensor assembly may include a linear potentiometer spanning the same distance as the tensile member 256, such that a length of the tensile member 256 can be measured, which can be extrapolated into a measured angle of the elbow joint 242 based on anthropomorphic measurements of the arm of the user 110. The sensor assembly 208 may also measure a tensile force of the tensile member 256 to determine an amount of strain or force being exerted upon the elbow joint 242 of the user 110 at any given point in time. Furthermore, a sensor of the sensor assembly 208 may measure one or more positions of one or more of the limb engaging members 204a and 204b, in relation to a hinge or joint at the elbow joint 242 of the user 110. For example, a sensor may measure an angle of the hinge between an upper arm limb engaging member 204a and a lower arm engaging member 204b. The angle of the hinge may be directly related to the angle of the elbow joint 242 of the user 110.

As with the other joint manipulation devices described herein, the signals associated with measurements of the force switches 206a and 206b, and/or and measurements of sensors from the sensor assembly 208 may be transmitted to device computing components 214 that may be operatively coupled to a portion of the joint manipulation device. In this example illustration in FIG. 2J, the device computing components 214 comprise a speaker 132 configured to receive command signals from one or more sensors of the joint manipulation device system 200 and/or from other components of the device computing components 214, where the command signals are configured to cause the speaker 132 to emit one or more audible alerts or notifications to the user 110 based on the operation of the joint manipulation device by the user 110, as described herein. As such, the speaker 132 may act as the indicator 212 of the joint manipulation device 202 in FIG. 2J.

One more non-limiting example of a joint manipulation device 202 is illustrated in FIG. 2K. The joint manipulation device 202 illustrated in FIG. 2K comprises a pronation and/or supination exercising device for a wrist and/or elbow of a user 110. In some embodiments, the joint manipulation device 202 of FIG. 2K may comprise one or more of the embodiments of the device described in U.S. patent application Ser. No. 14/569,627.

The joint manipulation device 202 of FIG. 2K may comprise a limb engaging member 204 with a first engaging side 204a and a second engaging side 204b. In particular, the limb engaging member 204 is configured to accept and engage a hand of a user 110, such that the palm and backside of the hand are engaged with one of the first engaging side 204a and the second engaging side 204b. One or more tensile members 256 may be operatively coupled to the limb engaging member 204, such that as the joint manipulation assembly 210 (e.g., a rotary device, a dial, etc. that is operatively coupled with the tensile member 256) moves the tensile member(s) 256 in one direction, the limb engaging member 204 rotates in that direction, causing either pronation or supination of the hand of the user 110. Because the illustrated joint manipulation device 202 is configured to operate in two directions, a first force sensor 206a may be operatively coupled to the first engaging side 204a of the limb engaging member 204, and a second force sensor 206b may be operatively coupled to the second engaging side 204b of the limb engaging member 204.

As such, the first force sensor 206a may be monitored by the joint manipulation device system 200 and/or the monitoring system 500 as when the first engaging side 204a of the joint manipulation device 202 is pressing against the hand of the user 110, causing either pronation or supination of the hand of the user 110. Likewise, the second force sensor 206b may be monitored when the second engaging side 204b of the joint manipulation device 202 is pressing against the hand of the user 110, causing either pronation or supination of the hand of the user 110.

As described with previous examples, one or more sensors in a sensor assembly 208 may be included in the joint manipulation device system 200 to measure one or more lengths of the tensile member 256 and/or tensile forces exerted on or by the tensile member 256. These measurements may be indicative of the user's 110 operation of the joint manipulation device 202, and therefore can be recorded and/or transmitted to the device computing components or other devices (e.g., the mobile device 300, the computing device 400, the monitoring system 500, and/or one or more third party systems 600).

In some embodiments, the sensor assembly 208 may comprise one or more accelerometers (not shown) operatively coupled to the limb engaging member 204. The accelerometers may measure and provide information associated with the movement of the limb engaging member 204 over a period of time to the device computing components and/or other devices. For example, the monitoring system 500 may simply monitor an accelerometer in the sensor assembly 208 to determine whether or not the joint manipulation device 202 is being operated. In some embodiments, the monitoring system 500 may also receive, from the sensor assembly 208, movement, acceleration, and positioning information associated with the limb engaging member 204 over time.

Again, the device computing components 214 may comprise a speaker 132 configured to provide one or more notifications or indications to the user 110 based on command signals received from the force sensors 206a and 206b, the sensor assembly 208, and/or one or more of the devices and systems in the system environment 100 (e.g., the mobile device 300, the computing device 400, the monitoring system 500, and/or one or more third party devices 600).

It should be noted that all of the example joint manipulation devices 202 illustrated in FIGS. 2G through 2K are one or more non-limiting possible configurations of the joint manipulation device 202 generally described in the system environment 100 of FIG. 1. Other configurations, both similar to the ones illustrated herein and dissimilar, are contemplated and envisioned herein. The examples provided are intended to provide a background for some of the types of joint manipulation devices 202, the sensors that may be comprised within a sensor assembly 208, and some of the possible joint manipulation assemblies 210 that may be utilized to achieve some of the embodiments of the invention.

FIG. 3 provides a block diagram illustrating a user's mobile device 300 of the system environment 100 of FIG. 1 in more detail, in accordance with embodiments of the invention. In one embodiment of the invention, the mobile device 300 is a mobile telephone. However, it should be understood that a mobile telephone is merely illustrative of one type of mobile device 300 that may benefit from, employ, or otherwise be involved with embodiments of the present invention and, therefore, should not be taken to limit the scope of embodiments of the present invention. Other types of mobile devices 300 may include wearable devices (e.g., smart watches, smart bracelets, smart glasses, etc.), portable digital assistants (PDAs), pagers, mobile televisions, gaming devices, laptop computers, cameras, video recorders, audio/video player, radio, GPS devices, or any combination of the aforementioned.

Some embodiments of the mobile device 300 include a processor 310 communicably coupled to such devices as a memory 320, user output devices 336, user input devices 340, a network interface 360, a power source 315, a clock or other timer 350, a camera 380, and a positioning system device 375. The processor 310, and other processors described herein, generally include circuitry for implementing communication and/or logic functions of the mobile device 300. For example, the processor 310 may include a digital signal processor device, a microprocessor device, and various analog to digital converters, digital to analog converters, and/or other support circuits. Control and signal processing functions of the mobile device 300 are allocated between these devices according to their respective capabilities. The processor 310 thus may also include the functionality to encode and interleave messages and data prior to modulation and transmission. The processor 310 can additionally include an internal data modem. Further, the processor 310 may include functionality to operate one or more software programs, which may be stored in the memory 320. For example, the processor 310 may be capable of operating a connectivity program, such as a web browser application 322. The web browser application 322 may then allow the mobile device 300 to transmit and receive web content, such as, for example, location-based content and/or other web page content, according to a Wireless Application Protocol (WAP), Hypertext Transfer Protocol (HTTP), and/or the like.

The processor 310 is configured to use the network interface 360 to communicate with one or more other devices on the network 150. In this regard, the network interface 360 includes an antenna 376 operatively coupled to a transmitter 374 and a receiver 372 (together a "transceiver"). The processor 310 is configured to provide signals to and receive signals from the transmitter 374 and receiver 372, respectively. The signals may include signaling information in accordance with the air interface standard of the applicable cellular system of the wireless telephone network 152. In this regard, the mobile device 300 may be configured to operate with one or more air interface standards, communication protocols, modulation types, and access types. By way of illustration, the mobile device 300 may be configured to operate in accordance with any of a number of first, second, third, and/or fourth-generation communication protocols and/or the like. For example, the mobile device 300 may be configured to operate in accordance with second-generation (2G) wireless communication protocols IS-136 (time division multiple access (TDMA)), GSM (global system for mobile communication), and/or IS-95 (code division multiple access (CDMA)), or with third-generation (3G) wireless communication protocols, such as Universal Mobile Telecommunications System (UMTS), CDMA2000, wideband CDMA (WCDMA) and/or time division-synchronous CDMA (TD-SCDMA), with fourth-generation (4G) wireless communication protocols, with LTE protocols, with 3GPP protocols and/or the like. The mobile device 300 may also be configured to operate in accordance with non-cellular communication mechanisms, such as via a wireless local area network (WLAN) or other communication/data networks.

The network interface 360 may also include a mobile device interface 370. The mobile device interface 370 may include software, such as encryption software, and hardware, such as a modem, for communicating information to and/or from one or more devices on a network 150 and connected with or that are part of the monitoring system 500. For example, the mobile device 300 may be configured so that it can be used as an interface for interacting with the joint manipulation device system 200 to receive information regarding the operation of the joint manipulation device 202 and/or to provide notes or instructions to the joint manipulation device system 200. Similarly, the mobile device interface 370 may be configured so that it can transmit information aggregated or derived from the mobile device (e.g., information and data associated with the operation of the joint manipulation device 202) to the monitoring system 500 or a third party system 600.

As described above, the mobile device 300 has a user interface that is, like other user interfaces described herein, made up of user output devices 336 and/or user input devices 340. The user output devices 336 include a display 330 (e.g., a liquid crystal display, LED display, or the like) and a speaker 332 or other audio device, which are operatively coupled to the processor 310. In some embodiments, the user output devices 336 includes one or more vibratory devices 334 that vibrate or otherwise move a portion or the entire mobile device 300 in response to certain command signals. For example, in embodiments where the mobile device 300 comprises a mobile phone, the mobile phone may receive command signals from the computing device components 214 of the join manipulation devices system 200, configured to cause the mobile phone to vibrate. Likewise, in embodiments where the mobile device 300 is a wearable device such as a smart watch, the wearable device may receive command signals from the computing device components 214 of the join manipulation devices system 200, configured to cause the mobile phone to vibrate.

In some embodiments of the invention, one or more of the user output devices 336, including the display 330, the speaker 332, and the vibratory device 334, may act as the indicator 212 of the joint manipulation device system 200.

The user input devices 340, which allow the mobile device 300 to receive data from a user such as the user 110, may include any of a number of devices allowing the mobile device 300 to receive data from the user 110, such as a keypad, keyboard, touch-screen, touchpad, microphone, mouse, joystick, other pointer device, button, soft key, and/or other input device(s). The user interface may also include a camera 380, such as a digital camera.

The mobile device 300 may also include a positioning system device 375 that is configured to be used by a positioning system to determine a location of the mobile device 300. For example, the positioning system device 375 may include a GPS transceiver. In some embodiments, the positioning system device 375 is at least partially made up of the antenna 376, transmitter 374, and receiver 372 described above. For example, in one embodiment, triangulation of cellular signals may be used to identify the approximate location of the mobile device 300. In other embodiments, the positioning system device 375 includes a proximity sensor or transmitter, such as an RFID tag, that can sense or be sensed by devices known to be located proximate the joint manipulation device system 200 or other location to determine that the mobile device 300 is located proximate these known devices.

The mobile device 300 further includes a power source 315, such as a battery, for powering various circuits and other devices that are used to operate the mobile device 300. Embodiments of the mobile device 300 may also include a clock or other timer 350 configured to determine and, in some cases, communicate actual or relative time to the processor 310 or one or more other devices. For example, in some embodiments, the clock 350 of the mobile device 300 is configured to provide timing information associated with the operation of the joint manipulation device system 200 by the user 110 (e.g., timing of exercises, duration of exercises, and the like).

The mobile device 300 also includes a memory 320 operatively coupled to the processor 310. As used herein, memory includes any computer readable medium (as defined herein below) configured to store data, code, or other information. The memory 320 may include volatile memory, such as volatile Random Access Memory (RAM) including a cache area for the temporary storage of data. The memory 320 may also include non-volatile memory, which can be embedded and/or may be removable. The non-volatile memory can additionally or alternatively include an electrically erasable programmable read-only memory (EEPROM), flash memory or the like.

The memory 320 can store any of a number of applications which comprise computer-executable instructions/code executed by the processor 310 to implement the functions of the mobile device 300 and/or one or more of the process/method steps described herein. For example, the memory 320 may include such applications as a conventional web browser application 322 and/or a joint manipulation device application 321. These applications also typically provide a graphical user interface (GUI) on the display 330 that allows the user 110 to communicate with the mobile device 300, the monitoring system 500, and/or other devices or systems (e.g., the joint manipulation device system 200, the computing device 400, and the third party systems 600). In one embodiment of the invention, when the user 110 is provided with a joint manipulation device system 200 that is associated with a software produce, the user may download, is assigned, or otherwise obtains the joint manipulation device application 321 from the monitoring entity 500, or from a distinct application server. In other embodiments, the user 110 interacts with the monitoring system 500 via the web browser application 322 in addition to, or instead of, the joint manipulation device application 321.

The memory 320 can also store any of a number of pieces of information, and data, used by the mobile device 300 and the applications and devices that make up the mobile device 300 or are in communication with the mobile device 300 to implement the functions of the mobile device 300 and/or the other systems described herein. For example, the memory 320 may include such data as user authentication information, anthropometric measurements of the user 110, target range of motion data associated with the user 110 and the associated joint manipulation device system 200, and the like.

Referring now to FIG. 4, the computing device 400 associated with the user 110 also includes various features, such as a network communication interface 410, a processing device 420, a user interface 430, and a memory device 450. The network communication interface 410 includes a device that allows the computing device 400 to communicate over the network 150 (shown in FIG. 1). In one embodiment of the invention, a network browsing application 455 provides for a user to establish network communication with a monitoring system 300 and/or a mobile device such as the mobile device 300 (shown in FIG. 1) for the purpose of receiving, storing, transmitting, displaying, and otherwise interacting with data and information associated with a joint manipulation device system 200 and a user's 110 operation and compliance therewith, in accordance with embodiments of the invention. Additionally, a joint manipulation device 456 may also receive, store, transmit, display, and otherwise interact with data and information associated with a joint manipulation device system 200 and a user's 110 operation and compliance therewith, in accordance with embodiments of the invention.

As used herein, a "processing device," such as the processing device 420, generally refers to a device or combination of devices having circuitry used for implementing the communication and/or logic functions of a particular system. For example, a processing device 420 may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device 420 may further include functionality to operate one or more software programs based on computer-executable program code thereof, which may be stored in a memory. As the phrase is used herein, a processing device 420 may be "configured to" perform a certain function in a variety of ways, including, for example, by having one or more general-purpose circuits perform the function by executing particular computer-executable program code embodied in computer-readable medium, and/or by having one or more application-specific circuits perform the function.

As used herein, a "user interface" 430 generally includes a plurality of interface devices and/or software that allow a customer (e.g., the user 110) to input commands and data to direct the processing device to execute instructions. For example, the user interface 430 presented in FIG. 4 may include a graphical user interface (GUI) or an interface to input computer-executable instructions that direct the processing device 420 to carry out specific functions. The user interface 430 employs certain input and output devices to input data received from the user 110 or an employee or agent of a monitoring entity associated with the monitoring system 500 or a third party system 600. These input and output devices may include a display, mouse, keyboard, button, touchpad, touch screen, microphone, speaker, LED, light, joystick, switch, buzzer, bell, and/or other customer input/output device for communicating with one or more customers. In some embodiments, the computing device 400 includes an indicator associated with the joint manipulation device system 200.

As used herein, a "memory device" 450 generally refers to a device or combination of devices that store one or more forms of computer-readable media for storing data and/or computer-executable program code/instructions. Computer-readable media is defined in greater detail below. For example, in one embodiment, the memory device 450 includes any computer memory that provides an actual or virtual space to temporarily or permanently store data and/or commands provided to the processing device 420 when it carries out its functions described herein.

FIG. 5 provides a block diagram illustrating the monitoring system 500, in greater detail, in accordance with embodiments of the invention. As illustrated in FIG. 5, in one embodiment of the invention, the monitoring system 500 includes one or more processing devices 520 operatively coupled to a network communication interface 510 and a memory device 550. In certain embodiments, the monitoring system 500 is operated by a first entity, such as a joint manipulation device product provider, while in other embodiments, the monitoring system 500 is operated by an entity other than a joint manipulation device product provider (e.g., a medical organization, an insurance organization, and the like).

It should be understood that the memory device 550 may include one or more databases or other data structures/repositories. The memory device 550 also includes computer-executable program code that instructs the processing device 520 to operate the network communication interface 510 to perform certain communication functions of the monitoring system 500 described herein. For example, in one embodiment of the monitoring system 500, the memory device 550 includes, but is not limited to, a network server application 570, a joint manipulation device application 580 which includes a mobile web server application 582 and user data 584, a third party application 590 which includes a mobile web server application 592, and other computer-executable instructions or other data. The computer-executable program code of the network server application 570, the joint manipulation device application 580, or the third party application 590 may instruct the processing device 520 to perform certain logic, data-processing, and data-storing functions of the monitoring system 500 described herein, as well as communication functions of the monitoring system 500.

In one embodiment, the user data 584 of the joint manipulation device application 580 may be data and information regarding the anthropometric measurements of one or more users 110, along with information regarding when a surgery took place, expected or target range of motion goals for the user 110 at certain periods of time, insurance information for one or more users 110, user 110 compliance with use of a joint manipulation device 202, and the like. The network server application 570, the joint manipulation device application 580, and the third party applications 590 can be configured to invoke or use the user data 584 and the mobile web server applications 582, 592, when monitoring a user's 110 operation of a joint manipulation device system 200, and the user's 110 compliance with standards, goals, instructions, and/or regulations for the joint manipulation device system 200.

As used herein, a "communication interface" generally includes a modem, server, transceiver, and/or other device for communicating with other devices on a network, and/or a user interface for communicating with one or more people (e.g., users 110, employees or agents of a monitoring entity, and the like). Referring again to FIG. 5, the network communication interface 510 is a communication interface having one or more communication devices configured to communicate with one or more other devices on the network 550, such as the joint manipulation device system 200, the mobile device 300, the computing device 400, and the other third party systems 600. The processing device 520 is configured to use the network communication interface 510 to transmit and/or receive data and/or commands to and/or from the other devices connected to the network 150.

Referring now to FIG. 6, a flowchart is provided to illustrate one embodiment of a process 600 for monitoring a user's compliance in operating a joint manipulation device, in accordance with embodiments of the invention. In some embodiments, the process 600 may include block 602, where the system provides a joint manipulation device to a user, comprising a joint manipulation device system, wherein the joint manipulation device is configured to exercise or stretch a joint of the user when under compliant conditions. The joint manipulation device may be provided to the user by a monitoring entity that is associated with a monitoring system. The joint manipulation device may be any device that is configured to engage with and/or manipulate at least a portion of a limb or joint of a user 110. The joint manipulation device may be one or more of the joint manipulation devices 202 described in more detail above, with respect to FIGS. 1 through 2K. Generally, the joint manipulation device comprises a limb engaging member (e.g., the limb engaging members 204), and a joint manipulation assembly (e.g., the joint manipulation assemblies 210).

The joint manipulation devices are configured to exercise or stretch a joint of a user by applying a force, via the joint manipulation assembly, to the limb engaging member, which thereby causes at least a portion of the user's limb to rotate about the joint being exercised or stretched. This also applies a rotational force to the joint of the user, which is intended to stretch out the muscle tissue, scar tissue (e.g., from a joint surgery), and ligaments of the joint of the user. However, the rotational force being applied to the joint of the user must be at a certain level for the stretching to be effective. Therefore, the monitoring entity may set a predetermined force or pressure threshold for the limb engaging member to exert upon the limb or joint of the user for a stretching incident to be considered in compliance with the standards or guidelines of the monitoring entity. These standards or guidelines may also be put in place by a third party individual or organization (e.g., a medical professional associated with the user).

In some cases, the stretching of a user's joint may be effective only if it occurs for at least a certain predetermined period of time (e.g., for 30 seconds, for 1 minute, for 10 minutes, for 1 hour, etc.). Additionally, the stretching regimen of the user may only be effective if the user rests for at least a predetermined period of time between stretching sessions (e.g., for 30 seconds, for 2 minutes, for 10 minutes, for 1 hour, etc.). Furthermore, the monitoring entity or a third party may determine that the user should use the joint manipulation device for a certain total period of time within an extended period of time (e.g., for 1 hour every day, for 5 hours every week, once every 8 hours, etc.). As such, the compliance data may include timing and/or duration data associated with what is expected to cause effective stretching of the user's joint to achieve a better range of motion of the joint.

In some embodiments, the process 600 includes step 604, where the system receives compliance data from the joint manipulation device system associated with compliant operation of the joint manipulation device by the user. The compliance data may comprise force data measured by one or more sensors of the joint manipulation device and/or timing data received from the joint manipulation device, as described above. However, in some embodiments, compliance data may comprise other types of data. For example, in some embodiments, general movement data (e.g., from a position sensor, from an accelerometer, etc.) may be comprised in the compliance data as an indication that the user has been operating the joint manipulation device.

The compliance data may be aggregated or analyzed within the joint manipulation device system (e.g., by device computing components like the device computing components 214), and/or the compliance data may be transmitted to the monitoring system or a third party system for aggregation and/or analysis.

Additionally, in some embodiments, the process 600 includes block 606, where the system provides an indication of a compliance status to the user at an indicator based on a comparison of the received compliance data and the compliant conditions. The indicator may be any type of indicator device that is configured to provide one or more alerts to the user based on the user's compliance status with the joint manipulation device. For example, the indicator may be the indicator 212 described above, a component of the device computing components 214 (e.g., the display 130, the speaker 132, and/or the vibratory device 134), a component of the mobile device 300 (e.g., the display 330, the speaker 332, and/or the vibratory device 334) described above, and/or the user interface 430 of the computing device 400.

When the system determines, based on the comparison of the received compliance data (i.e., the force or pressure data, the timing data, the duration data, the general movement data, etc.), with the predetermined compliant conditions (e.g., the required or suggested force threshold values, the required or suggested duration, resting, and frequency timing specifications, etc.), that the user's operation of the joint manipulation device is in a compliant status, the system may transmit one or more command signals configured to cause the indicator to emit or provide a first alert to the user. For example, the system may transmit a command signal configured to cause a speaker associated with the joint manipulation device system and/or a mobile or general computing device of the user to emit a first alert tone (e.g., a single beep, a single tone, a voice notification, etc.) that is associated with a compliant usage status. This allows the user to know that the user's operation of the joint manipulation device is currently in compliance with the standards or guidelines for the device. Of course, the indication to the user may come in the form of a visual alert (e.g., by a flashing LED, by an LED emitting a certain color of light, by a visual display notification, etc.), a vibratory alert, or any combination of an audible, visual, and/or vibratory alert.

Likewise, when the system determines, based on the comparison of the received compliance data with the predetermined compliant conditions, that the user's operation of the joint manipulation device is not currently compliant, the system may transmit one or more command signals configured to cause the indicator to emit or provide a second alert to the user. For example, the system may transmit a command signal configured to cause the speaker to emit a second alert tone (e.g., a pair of beeps, a single tone, a voice notification, etc.) that is associated with a non-compliant usage status. Again, the system utilize an audible indicator, a visual indicator, a vibratory indicator, or any combination thereof to provide the alert to the user.

In some embodiments, the system may determine that the user is close to falling out of a compliant status, based on the received compliance data. For example, the system may determine that the received force data has fallen below the predetermined threshold for less than a predetermined period of time that would cause the user's operation of the joint manipulation device to fall out of compliance. The system could then cause the indicator to transmit a third alert to the user that is associated with a warning of potential non-compliance of the user's operation of the joint manipulation device. This would allow the user to make any necessary changes to the joint manipulation device to put the user's operation of the device back in compliance with the compliant conditions.

The system may also track the duration of the user's compliant use of the joint manipulation device and cause the indicator(s) to provide a "finished" notification when the user has operated the joint manipulation device in a compliant status for the suggested or required duration of the monitoring entity or a third party's standards.

The system may additionally or alternatively include a tiered notification process to the user. In this way, the system may introduce gamification principles to incentivize the user to remain compliant with the operation of the joint manipulation device, or otherwise better understand the user's progress in recovery. For example, the system may provide a notification to the user to inform the user what percentage of the exercise (either the current exercise or the total set of exercises needed to fully recover) has been completed and/or remains. The system may also inform the user of increases in the amount of force being applied to the limb of the user and/or the increases in the range of motion of the joint of the user, as the user progresses to more rigorous exercising ranges or levels. For example, in response to determining that the user has remained compliant for exercising a leg with a first manipulation force amount for a necessary period of time, the system may determine that the user should now progress to a second, higher, manipulation force amount. Therefore, the system may transmit a notification to the user (e.g., via the joint manipulation device system, the mobile device of the user, and/or the computing device of the user) that informs the user that the user has now achieved a higher rank. The notification may be in any form described herein, including, but not limited to, displaying a color, displaying a text notification, emitting an audible beep, emitting an audible message, emitting a vibration, any combination of the above, and the like.

The process 600 may also include block 608, where the system receives progress data associated with a range of motion of the joint of the user, wherein the progress data comprises at least one of pressure data, force data, time data, and range of motion data. The range of motion data comprises any data and measurements associated with the amount of rotation of the joint being exercised or stretched by the joint manipulation device, including the minimum and maximum angles of rotation achieved during a stretching incident, total or average forces exerted upon the limb and/or joint of the user during a stretching incident, and the like. The pressure data and force data may be associated with the amount(s) of force applied by the joint manipulation device over the period of time that the device was in use. The time data may include the duration of the joint exercise or stretch, as well as any frequency of stretching data, time of day data, and the like.

Together, the progress data provides an overview of how the user operated the joint manipulation device and how the joint manipulation device affected the limb(s) and/or joint of the user during one or more stretching or exercise incidents. This data is indicative of the level of exercise or stretching that the user's joint endured, and can be used to track a user's progress in increasing the user's range of motion for the injured joint of the user over time.

In some embodiments, the system may measure and/or receive data from multiple sources. For example, the system may be configured to receive measurement data from a first sensor, measurement data from a second sensor, user medical information from a first data stream, biometric data of the user from a second data stream, user compliance requirement data from a third data stream, and the like. The system may then compile this data to make determinations regarding the user's operation of the joint manipulation device, such as whether the user is remaining compliant, whether the joint manipulation device is being effective, and the like.

As such, and in some embodiments, the process 600 includes block 610, where the system aggregates the received progress data into effectiveness data, excluding progress data collected during a period of non-compliant use of the joint manipulation device by the user. By removing or otherwise excluding the data that was obtained during a period of time when the user's operation of the joint manipulation device was not in compliance with the compliant conditions, the system can compile a useful dataset of joint exercising and stretching information, and its results on improving the range of motion of the joint over time, without diluting the dataset with inappropriate data. For example, if a user did not fully engage the user's limb with enough force or pressure to meet the threshold force requirement of the compliant conditions, then the joint manipulation device would not be expected to improve the range of motion of the user's joint as intended. Therefore, excluding the non-compliant data from the effectiveness dataset provides a comprehensive and accurate dataset of the joint manipulation device's actual effectiveness in improving the range of motion for a user.

Finally, in some embodiments, the process 600 includes block 612, where the system transmits the effectiveness data to one or more third party systems. The effectiveness data, as described above, is an accurate and comprehensive aggregation of data associated with a user's operation of a joint manipulation device within compliant conditions, as set by a monitoring entity or a third party entity. Therefore, this data can be especially helpful in providing patient compliance data to an insurance organization (e.g., a medical insurer after the user has surgery on the user's joint, a workers compensation insurer, etc.) for reimbursement purposes, and otherwise. This data transfer is especially helpful due to the fact that the effectiveness data can be transmitted directly from the joint manipulation device system to the third party system over a network (e.g., the network 150), or via the monitoring system with little-to-no individual agent intervention or overview, thereby significantly reducing the man-hours would otherwise take to receive, compile, filter, and transfer the effectiveness and/or compliance data to one or more third parties.

Additionally, the effectiveness data can be utilized by the monitoring entity or a third party entity for research purposes to analyze and develop the most effective compliance standards for a joint manipulation device. For example, a research project may comprise adjusting the force thresholds and/or timing or duration requirements of the compliant conditions to determine the lowest force or pressure thresholds and/or the shortest duration or timing requirements for the joint manipulation device to be considered effective in improving the range of motion of a user's joint. By removing the non-compliant data as described herein, the researching entity can maintain an accurate set of data that is actually compliant with the intended or suggested stretching or exercise parameters of the joint manipulation device without requiring individuals from the research entity to physically monitor the use of the device in person.

As discussed above, in some embodiments, a joint manipulation device may be configured to communicate with a mobile device or other computing device or monitor (e.g., one or more sensors) associated with the user, such that the device can transmit information about the user's operation of the joint manipulation device and the user's progress in conducting exercises with the joint manipulation device over a period of time. In some embodiments, the communication channel for such communications may be or include a direct connection between a communication device that is part of and/or operably connected with the joint manipulation device. In other embodiments, the communication channel may be or include an indirect connection over a network such as the Internet and/or one or more other networks, such as WANs, LANs or the like, with the mobile device application and/or a server application. In some embodiments, a server or group of servers are configured to receive and aggregate data from one or multiple communication devices associated with one or more joint manipulation devices. In some embodiments, the communication devices are not necessarily connected to a joint manipulation device, but rather serve as a data acquisition tool, configured to accept data entry from one or more users or caretakers or to monitor and/or sense conditions or characteristics without being connected to a joint manipulation device. In some such embodiments, the communication device may store the data until it is uploaded, either by remote connection and control, or by download to a locally connected device.

In some embodiments, a user (patient or caregiver) has a mobile device with an application or "app" installed thereon. The app may be a stand-alone application requiring no connection to a joint manipulation device, but rather relying on patient self-reporting of progress toward goals. In some embodiments of the app, an administrator may set certain thresholds for progress, and the app can generate graphs illustrating patient progress toward goals. Alternatively, the app may facilitate a connection with a communication device of the joint manipulation device, over direct connection or indirect communication channel.

The app may be configured to control data collection from the joint manipulation device. In other words, the app may send control signals from the mobile device to the communication device that is operably connected with one or more monitors or sensors. The app may thereby cause the monitors/sensors to collect certain types of data or characteristics and may control parameters of such collection, such as time of collection or the like. In some embodiments, the app may send control signals to the communication device to cause some manipulation of the joint manipulation device itself. Such control signals may be based on timing, patient progress, or otherwise.

In one example, the data transmitted by the joint manipulation device may populate in a mobile application installed on the mobile device of the user (or installed on a third party server and accessed at a web page). In this way, the user can view details of specific joint exercises and/or the user's progress over time in using the joint manipulating device to stretch and exercise the user's joint.

In some embodiments, the user can set one or more thresholds for patient achievement. As shown in FIG. 7A, a chart illustrates a hypothetical patient's range of motion progress over time using a joint manipulation device (in this example a knee manipulation device) as contemplated herein. As shown, a measurement indicating an amount of knee flexion is collected by one or more monitors, and may be communicated via a communication device to the app on a mobile device. The mobile device app may generate a chart similar to the one shown in FIG. 7A to communicate progress information to the patient or caregiver. The app may illustrate thresholds of knee flexion that generally correspond to milestones of progress, such as walking, navigating stairs, rising from a chair, tying shoes, and the like. Such threshold of progress may be modified by an administrator of the app, such as a treating physician, the app developer, the caregiver, or in certain cases, the patient.

As illustrated in FIG. 7B, a chart illustrates a score (e.g., the PROMIS Score), which is an indication of patient progress toward a goal, such as the ultimate goal of normal flexion or extension of a joint. Progress thresholds may be set by an administrator of the app, such as a treating physician, the app developer, the caregiver, or in some cases, the patient. In the example shown, the progress score is charted over time and illustrated in relation to thresholds such as moderate satisfaction, normal population average, and extremely satisfied thresholds. The PROMIS score is a standardized scoring system. The acronym stands for Patient-Reported Outcomes Measurement Information System, which represent dynamic tools to measure health outcomes from the patient perspective. Other scoring systems may be used in various embodiments.

The application is typically implemented in conjunction with a patient conversation about the app. There may be, for example, an app setup questionnaire that includes questions such as "Did you understand the training you received?" and "Do you need someone to call you?" Such questionnaire may be given the patient via tradition means or may be performed over the app and the results collected and analyzed.

There may also be a standard questionnaire, either presented traditionally or over the app, that may include, for example, questions related to manually reporting of patient progress information such as "Since you last reported, do you feel like you have gained range of motion?", "Since you last reported, what is the average number of stretching sessions you have completed each day?", "On average, how many minutes have you stretched per session?", "Do you need someone to call you?", and "Have there been any significant events in your recovery (additional surgical procedure, scheduled procedure, return to work, etc.)?"

There may also be a "PROMIS" patient questionnaire presented to the patient, which may include questions such as "Are you able to do chores such as vacuuming or yard work?", "Are you able to go up and down stairs?", "Are you able to walk at least 15 minutes?", "Are you able to run errands and shop?", "Does your health now limit you in doing two hours of physical labor?", "Does your health now limit you in doing moderate work around the house like vacuuming, sweeping floors or carrying groceries?", "Does your health now limit you in lifting of carrying groceries?", and "Does your health now limit you in doing heavy work around the house like scrubbing floors, or lifting or moving heavy furniture?"

The app may include pictures and/or graphs illustrating progress toward certain goals or thresholds as illustrated in FIGS. 7A and 7B.

The patient may also receive a final questionnaire, which may include questions such as "Are you satisfied with the app?", "Would you recommend the program to a friend?", and "Would you be willing to provide a testimonial?".

An example timeline for use of the app by a patient is discussed below. The patient's smart phone or mobile device downloads and installs the app and a technician or caregiver typically logs the patient into the app and the patient changes her password. Use of the app on an example schedule may proceed as follows:

Day 0
  1. Promis
  2. Picture(s)
Day 1
  1. Setup questionnaire
Day 11
  1. Standard Questionnaire
Day 20
  1. Promis
  2. Picture(s)
Day 35
  1. Standard Questionnaire
Day 50
  1. Promis
  2. Picture(s)
Day65
  1. Standard Questionnaire
Day 80
  1. Promis
  2. Picture(s)
Day 95
  1. Standard Questionnaire
Day 100
  1. Promis 2. Picture(s)

Continue pattern until the device is triggered to be picked up

1. End protocol
2. Final Questionnaire

In some embodiments, the physical therapist and/or physician has an app that is tied to the patient app such that the PT or MD has access to the patient progress data. In some embodiments, an insurance adjuster has an app and access to the patient progress data. In some embodiments, the app may be programmed to provide alerts to the patient, the caregiver, or other interested party. For example, the app may be programmed to provide an alert that the patient has logged into the app to other interested parties, such as PT, MD or adjuster. In some embodiments, the app asks the patient the frequency that the patient wants to be surveyed, and in some embodiments the patient has the ability to upload a video testimonial and/or videos of use of the joint manipulation device as the patient progresses.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, and the like), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s).

The computer-executable program code may also be loaded onto a computer or other programmable data processing apparatus to cause a series of operational steps to be performed on the computer or other programmable apparatus to produce a computer-implemented process such that the code portions which execute on the computer or other programmable apparatus provide steps for implementing the functions/acts specified in the flowchart and/or block diagram block(s). Alternatively, computer program implemented steps or acts may be combined with operator or human implemented steps or acts in order to carry out an embodiment of the invention.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

Embodiments of the present invention are described above with reference to flowcharts and/or block diagrams. It will be understood that steps of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

The invention claimed is:

1. A system for measuring and monitoring a joint manipulation device system, the system comprising:
    one or more memory devices; and
    one or more processing devices operatively coupled to the memory device, wherein the one or more processing devices are configured to execute computer-readable computer program code to:
        receive compliance data corresponding to a joint manipulation device system associated with compliant operation of a joint manipulation device by a user;
        compare the received compliance data with predetermined compliant conditions;
        receive progress data corresponding to the joint manipulation device system, wherein the progress data comprises at least one of pressure data, force data, time data, and range of motion data associated with a joint of the user;
        aggregate the received progress data into effectiveness data, wherein progress data collected during a period of non-compliance is excluded from the effectiveness data; and
        in response to aggregating the received progress data into effectiveness data, transmit the effectiveness data to one or more third party systems.

2. The system of claim 1, wherein the one or more processing devices are further configured to execute computer-readable computer program code to:
    provide an indication of a compliant status to the user at an indicator based on the comparison of the received compliance data and the predetermined compliant conditions.

3. The system of claim 2, wherein providing an indication of a compliant status to the user at an indicator based on the comparison of the received compliance data and the predetermined compliant conditions further comprises:
    determining that the received compliance data does not meet the predetermined compliant conditions; and
    transmitting control signals configured to cause a speaker device associated with the joint manipulation device system to emit a first audible alert to the user, wherein the first audible alert is associated with non-compliant use of the joint manipulation device.

4. The system of claim 2, wherein providing an indication of a compliant status to the user at an indicator based on the comparison of the received compliance data and the predetermined compliant conditions further comprises:
    determining that the received compliance data does meet the predetermined compliant conditions; and
    transmitting control signals configured to cause a speaker device associated with the joint manipulation device system to emit a second audible alert to the user, wherein the second audible alert is associated with compliant use of the joint manipulation device.

5. The system of claim 1, wherein the one or more processing devices are further configured to execute computer-readable computer program code to:
    compare the effectiveness data with predetermined goals associated with compliance of the user in operating the joint manipulation device;
    determine, based on the comparison, that a feature of the joint manipulation device needs to be adjusted to meet one of the predetermined goals;
    in response to determining that the feature needs to be adjusted, transmitting control signals configured to cause the joint manipulation device to adjust the feature.

6. The system of claim 1, wherein the one or more processing devices are further configured to execute computer-readable program code to:
    receive input from the one or more third party systems, wherein the input comprises a recommendation to adjust a feature of the joint manipulation device to maintain compliance from a medical professional associated with the user;
    in response to receiving the input, transmit control signals configured to cause the joint manipulation device to adjust the feature or to cause communication of a notification to a device technician to adjust the feature.

7. The system of claim 1, wherein the compliance data comprises at least a pressure exerted between a limb engaging member of the joint manipulation device and a portion of a limb of the user associated with the joint of the user.

8. The system of claim 7, wherein the compliance data meets the predetermined compliant conditions when the pressure exerted between the limb engaging member of the joint manipulation device and the portion of the limb of the user associated with the joint of the user is at or above a predetermined threshold pressure value.

9. The system of claim 1, wherein the range of motion data comprises a minimum and a maximum degree of rotation for the joint of the user, as measured by one or more sensors of the joint manipulation device system.

10. The system of claim 1, wherein the time data comprises one or more periods of time during which the joint manipulation device system was operated in compliance with the predetermined compliant conditions.

11. The system of claim 1, wherein the effectiveness data is transmitted to one or more doctors, physical therapists, or insurance provider organizations associated with the user or the joint manipulation device system.

12. The system of claim 1, wherein the compliance data and the progress data are received from the joint manipulation device system.

13. The system of claim 1, wherein the system comprises a mobile device running an application for receiving the compliance data and progress data as inputs self-reported by the user.

14. The system of claim 13, wherein the range of motion data comprises a minimum and a maximum degree of rotation for the joint of the user, as measured from one or more pictures taken by the user using the application running on the mobile device.

15. A device for manipulation of a joint of a limb of a user and for measuring at least one aspect of the manipulation, wherein the device comprises:
    a limb engaging member;
    a joint manipulation assembly;

one or more sensors configured to measure manipulation of the joint of the user, wherein the one or more sensors comprise one or more force sensors configured to measure a force exerted by the limb of the user on at least a portion of the device;
a communication device operatively connected to the one or more sensors, the communication device configured to transmit measurements through a network to an application running on a mobile device of a user, and
a speaker device configured to emit a first audible alert when the force exerted by the limb of the user is below a predetermined threshold value, and wherein the speaker device is configured to emit a second audible alert when the force exerted by the limb of the user is above the predetermined threshold value.

16. The device of claim 15, wherein the device further comprises:
a pressure switch operatively coupled to the limb engaging member or the joint manipulation assembly comprising a first orientation associated with a measured pressure of less than a predetermined pressure threshold, and a second orientation associated with a measured pressure equal to or greater than the predetermined threshold, wherein: in the first orientation, electronic components of the device are turned off or are in a low energy mode; and
in the second orientation, the electronic components of the device are turned on or are in an operational mode.

17. The device of claim 15, wherein the one or more sensors comprise:
one or more angle sensors configured to measure an angle of the joint.

18. The device of claim 15, wherein the one or more sensors comprise:
one or more position sensors configured to measure a position of at least a portion of the limb relative to the one or more position sensors.

19. The device of claim 15, wherein the joint manipulation assembly adjusts a position of at least a portion of the limb relative to the measured force exerted by the limb of the user.

20. The device of claim 15, wherein the joint manipulation assembly adjusts a resistive force applied to at least a portion of the limb relative to the measured force exerted by the limb of the user.

21. The device of claim 15, wherein the joint manipulation assembly adjusts an angle of the joint relative to the measured force exerted by the limb of the user.

22. The device of claim 15, wherein the device further comprises:
a display, wherein the display can be configured to present one or more notifications to the user, wherein in response to a measurement of the one or more sensors configured to measure manipulation of the joint of the user, the display presents a request for at least a portion of the joint manipulation device to be adjusted by the user.

23. The device of claim 15, wherein the device further comprises:
a data acquisition system configured to acquire data associated with the joint manipulation assembly and the one or more sensors.

24. The device of claim 23, wherein the data acquisition system is configured to transmit the acquired data to one or more monitoring systems.

25. A method for measuring and monitoring a joint manipulation device, the method comprising:
receiving force data comprising at least a force value from a force sensor associated with a limb engaging portion of a joint manipulation device;
determining that if the force value is below a force threshold value and causing electronic components of the joint manipulation device to operate in a low energy state; and determining that if the force value is equal or above the force threshold value and causing the electronic components of the joint manipulation device to operate in a data collection and transmission state, wherein while the force value is equal to or above the force threshold value, the method further comprises:
causing an indicator to operate in a first configuration associated with proper use of the joint manipulation device;
acquiring, from one or more position sensors, positional information associated with the joint manipulation device;
acquiring timing information associated with the joint manipulation device; and
transmitting, from one or more communication devices associated with the joint manipulation device, the acquired positional information and timing information to a monitoring system.

26. A system for measuring and monitoring user compliance with a joint manipulation device comprising:
at least one limb engaging member;
one or more electronic components operatively coupled to the at least one limb engaging member;
a joint manipulation assembly operatively coupled to the at least one limb engaging member; and
a force switch operatively coupled to the at least one limb engaging member, wherein the force switch is configured to be in a first orientation in response to measuring a force amount below a threshold value, and wherein the force switch is configured to be in a second orientation in response to measuring a force amount that is at or above the threshold value;
said system comprising:
one or more memory devices having computer readable program code stored thereon;
a communication device; and
one or more processing devices operatively coupled to the one or more memory devices, wherein the one or more processing devices are configured to execute the computer readable program code to:
in response to determining that the force switch has altered from the first orientation to the second orientation, cause electronic components of the joint manipulation device to adjust from an off state or a low power state to an on state or an operational state.

27. A system for measuring and monitoring a joint manipulation device system, the system comprising:
one or more memory devices; and
one or more processing devices operatively coupled to the memory device, wherein the one or more processing devices are configured to execute computer-readable computer program code to:
receive compliance data from a joint manipulation device system associated with compliant operation of a joint manipulation device by a user;
compare the received compliance data with predetermined compliant conditions;
determine, based on the comparison of the received compliance data with the predetermined compliant conditions, whether the joint manipulation device is currently compliant with the predetermined compliant conditions;

in response to determining that the joint manipulation device is currently compliant with the predetermined compliant conditions, transmit control signals configured to cause a speaker associated with the joint manipulation device to emit an audible alert representing the compliant operation of the joint manipulation device; and in response to determining that the joint manipulation device is currently not compliant with the predetermined compliant conditions, transmit control signals configured to cause the speaker associated with the joint manipulation device to emit an audible alert representing the not compliant operation of the joint manipulation device.

* * * * *